United States Patent
Carson et al.

(10) Patent No.: US 9,128,032 B2
(45) Date of Patent: Sep. 8, 2015

(54) THREE-DIMENSIONAL STARING SPARE ARRAY PHOTOACOUSTIC IMAGER AND METHODS FOR CALIBRATING AN IMAGER

(75) Inventors: Jeffrey J. L. Carson, London (CA); Pinhas Ephrat, London (CA); Lynn Keenliside, Lucan (CA); Michael Barret Roumeliotis, London (CA)

(73) Assignee: MULTI-MAGNETICS INCORPORATED, London (CA)

( * ) Notice: Subject to any disclaimer, the term of this patent is extended or adjusted under 35 U.S.C. 154(b) by 396 days.

(21) Appl. No.: 12/814,086

(22) Filed: Jun. 11, 2010

(65) Prior Publication Data

US 2010/0249570 A1 Sep. 30, 2010
US 2013/0338474 A9 Dec. 19, 2013

Related U.S. Application Data

(63) Continuation of application No. PCT/CA2008/002177, filed on Dec. 12, 2008.

(60) Provisional application No. 61/013,127, filed on Dec. 12, 2007.

(51) Int. Cl.
*A61B 5/05* (2006.01)
*G01N 29/24* (2006.01)
(Continued)

(52) U.S. Cl.
CPC .......... *G01N 29/2418* (2013.01); *A61B 5/0059* (2013.01); *A61B 5/0095* (2013.01);
(Continued)

(58) Field of Classification Search
CPC . A61B 5/0095; G01N 29/30; G01N 29/2418; G01N 29/0654; G01N 2291/106
USPC ........................................................ 600/437
See application file for complete search history.

(56) References Cited

U.S. PATENT DOCUMENTS

| 4,255,971 A | 3/1981 | Rosencwaig |
| 4,543,486 A | 9/1985 | Rose |

(Continued)

FOREIGN PATENT DOCUMENTS

| CA | 2187701 A1 | 4/1998 |
| CA | 2361076 A1 | 8/2000 |

(Continued)

OTHER PUBLICATIONS

Kruger et al, Thermoacoustic computed tomography using a conventional linear transducer array, Medical Physics 30, 856 (2003).*

(Continued)

*Primary Examiner* — Unsu Jung
*Assistant Examiner* — Serkan Akar
(74) *Attorney, Agent, or Firm* — Gifford, Krass, Sprinkle, Anderson & Citkowski, P.C.

(57) ABSTRACT

A photoacoustic imaging apparatus is provided for medical or other imaging applications and also a method for calibrating this apparatus. The apparatus employs a sparse array of transducer elements and a reconstruction algorithm. Spatial calibration maps of the sparse array are used to optimize the reconstruction algorithm. The apparatus includes a laser producing a pulsed laser beam to illuminate a subject for imaging and generate photoacoustic waves. The transducers are fixedly mounted on a holder so as to form the sparse array. A photoacoustic (PA) waves are received by each transducer. The resultant analog signals from each transducer are amplified, filtered, and converted to digital signals in parallel by a data acquisition system which is operatively connected to a computer. The computer receives the digital signals and processes the digital signals by the algorithm based on iterative forward projection and back-projection in order to provide the image.

27 Claims, 27 Drawing Sheets

(51) Int. Cl.
*A61B 5/00* (2006.01)
*G01N 29/06* (2006.01)
*G01N 29/30* (2006.01)
*G06F 19/00* (2011.01)
*A61B 8/08* (2006.01)

(52) U.S. Cl.
CPC ............ *G01N29/0654* (2013.01); *G01N 29/30* (2013.01); *A61B 8/483* (2013.01); *G01N 2291/106* (2013.01)

(56) References Cited

U.S. PATENT DOCUMENTS

| | | | |
|---|---|---|---|
| 5,070,733 | A | 12/1991 | Nagata et al. |
| 5,230,339 | A | 7/1993 | Charlebois |
| 5,275,052 | A | 1/1994 | Luttrell et al. |
| 5,435,312 | A | 7/1995 | Spivey et al. |
| 5,713,356 | A | 2/1998 | Kruger |
| 5,781,294 | A | 7/1998 | Nakata et al. |
| 5,840,023 | A | 11/1998 | Oraevsky et al. |
| 6,104,942 | A | 8/2000 | Kruger |
| 6,216,025 | B1 | 4/2001 | Kruger |
| 6,309,352 | B1 | 10/2001 | Oraevsky et al. |
| 6,475,150 | B2 | 11/2002 | Haddad |
| 6,490,470 | B1 * | 12/2002 | Kruger ........................... 600/407 |
| 6,503,204 | B1 | 1/2003 | Sumanaweera et al. |
| 6,511,433 | B1 | 1/2003 | Benjamin |
| 6,524,253 | B1 | 2/2003 | Abend |
| 6,567,688 | B1 | 5/2003 | Wang |
| 6,582,367 | B1 | 6/2003 | Robinson et al. |
| 6,633,774 | B2 * | 10/2003 | Kruger ........................... 600/407 |
| 6,672,165 | B2 | 1/2004 | Rather et al. |
| 6,783,497 | B2 * | 8/2004 | Grenon et al. ................ 600/459 |
| 7,266,407 | B2 * | 9/2007 | Li et al. ........................... 600/430 |
| 7,821,704 | B1 * | 10/2010 | Pepper et al. .................. 359/344 |
| 2002/0193678 | A1 | 12/2002 | Kruger |
| 2003/0220554 | A1 | 11/2003 | Grenon et al. |
| 2004/0039379 | A1 * | 2/2004 | Viator et al. ...................... 606/9 |
| 2004/0122316 | A1 | 6/2004 | Satoh |
| 2005/0090725 | A1 | 4/2005 | Page et al. |
| 2005/0203370 | A1 | 9/2005 | Patch |
| 2006/0027021 | A1 * | 2/2006 | Choi et al. ........................ 73/579 |
| 2006/0184042 | A1 * | 8/2006 | Wang et al. ................... 600/476 |
| 2007/0238958 | A1 * | 10/2007 | Oraevsky et al. ............. 600/407 |
| 2008/0173093 | A1 | 7/2008 | Wang et al. |
| 2008/0221647 | A1 | 9/2008 | Chamberland et al. |

FOREIGN PATENT DOCUMENTS

| | | |
|---|---|---|
| EP | 1279385 A1 | 1/2003 |
| WO | 0045707 A2 | 8/2000 |
| WO | 2007094771 A1 | 8/2007 |

OTHER PUBLICATIONS

Vaithilingam et al, A Co-axial Scanning Acoustic and Photoacoustic Microscope, 2007 IEEE Ultrasonics Symposium.*
Wang et al, Photoacoustic imaging with deconvolution algorithm, Phys. Med. Biol. 49, 2004, pp. 3117-3124.*
Paltauf et al, Iterative reconstruction method for three-dimensional optpacoustic imaging, SPIE, 2001, 138-146, vol. 4256.
Extended Search Report—International Application EP08859007.

* cited by examiner

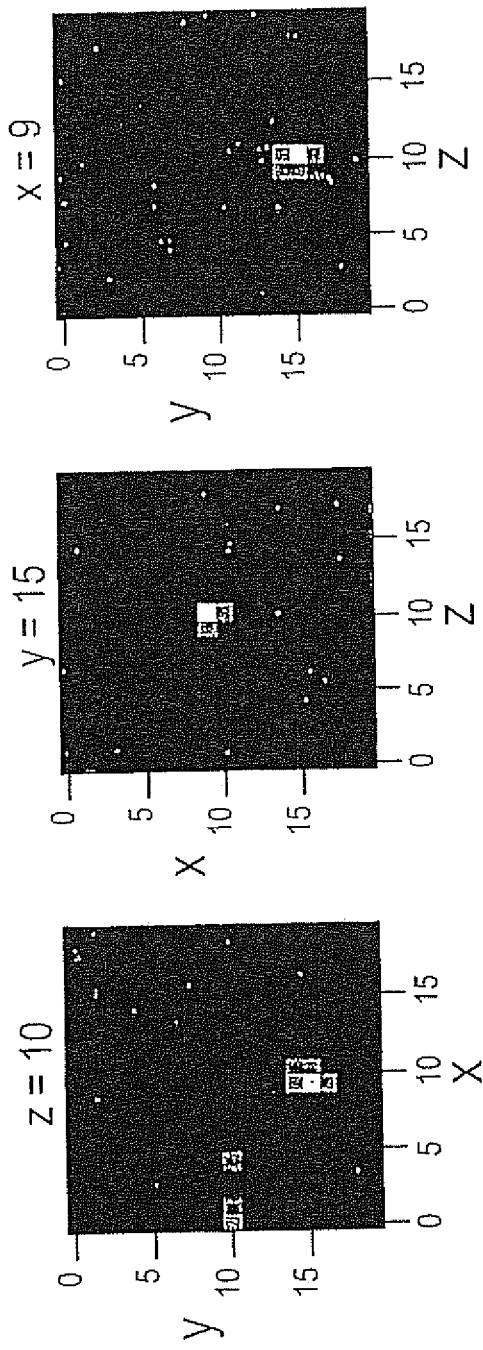

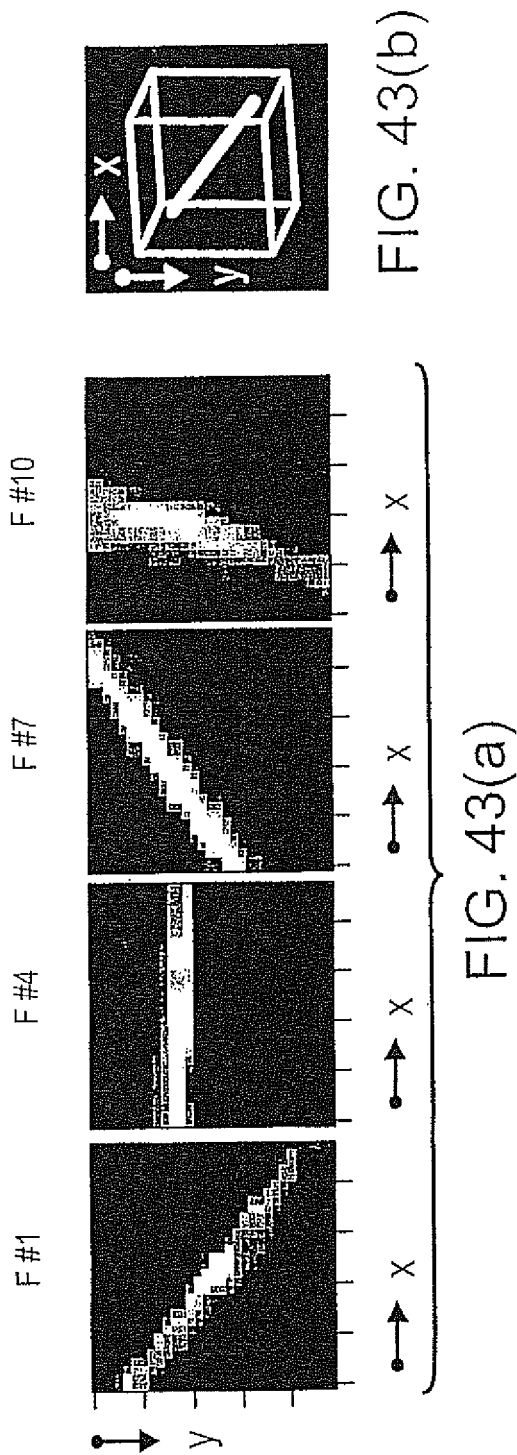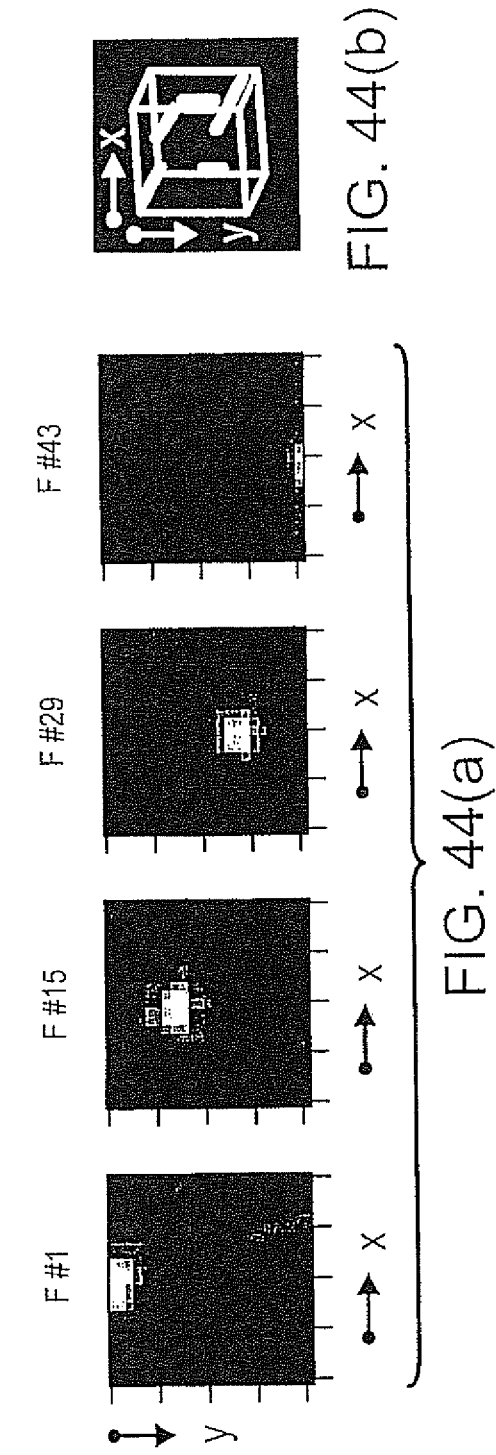
FIG. 43(a)  FIG. 43(b)
FIG. 44(a)  FIG. 44(b)

THREE-DIMENSIONAL STARING SPARE ARRAY PHOTOACOUSTIC IMAGER AND METHODS FOR CALIBRATING AN IMAGER

PRIOR APPLICATIONS

This application is a continuation of International PCT Application No. PCT/CA2008/002177 filed Dec. 12, 2008 which claims priority of U.S. Provisional Patent Application No. 61/013,127 filed Dec. 12, 2007.

BACKGROUND OF THE INVENTION

This invention relates to apparatus for photoacoustic (PA) imaging of structures in an optically absorbing subject and methods and apparatus for calibrating an imaging apparatus of this type. These types of imaging apparatus and methods can be useful for medical, scientific, and industrial imaging, imaging of physiological parameters and tracking of molecular probes.

Photoacoustic (PA) imaging is a method to visualize distribution of optically absorbing objects in a volume of interest. The method employs short laser pulses that illuminate the volume and cause the absorbing objects to heat up slightly and undergo thermoelastic expansion which results in outward-propagating pressure waves. By measuring the time-of-flight and profile of these pressure waves at points outside the volume, and then applying back-projection algorithms, the location and relative strengths of the photoacoustic sources can be deduced. Many approaches have been suggested for three-dimensional PA imaging. Each employs a different combination of detection scheme and image reconstruction algorithm. These can be divided into scanning methods, where a single detector is scanned along the detection surface in two dimensions and staring methods, where a 2D array of detectors is used and no scanning is necessary. A combined scanning-staring approach has been suggested as well, where a linear array of detectors is scanned in one dimension. Several methods for 3-D PA image reconstruction have been proposed as well, including the spherical Radon transform, synthetic aperture beam forming, plane-wave approximation, iterative back-projection and universal closed-form radial back-projection. It has also been shown that detector(s) line of sight toward the PA source defined the source boundaries that can be sharply reconstructed. In other words, the wider the range of viewing angles subtended by the detector(s) toward the imaging volume, the better defined the reconstructed images would be.

U.S. Pat. No. 5,713,356 to Kruger teaches methods and apparatus for measuring and characterizing the localized electromagnetic wave absorption properties of biologic tissues in vivo using incident electromagnetic waves to produce resultant acoustic waves. Multiple acoustic transducers are acoustically coupled to the surface of the tissue for measuring acoustic waves produced in the tissue when the tissue is exposed to a pulse of electromagnetic radiation. The multiple transducer signals are then combined to produce an image of the absorptivity of the tissue, which image may be used for medical diagnostic purposes. In specific embodiments, the transducers are moved to collect data from multiple locations, to facilitate imaging. In a subsequent patent to Kruger, namely U.S. Pat. No. 6,104,942, Kruger indicates that in the method described in U.S. Pat. No. 5,713,356, a large number of pulses of electromagnetic radiation (e.g. 100-100,000) spaced at a repetition interval, are generated to stimulate the tissue.

U.S. Pat. No. 5,840,023 to Oraevsky entitled "Optoacoustic Imaging for Medical Diagnosis" describes a system that utilizes time-resolved measurement of profiles of laser-induced transient pressure (acoustic) waves. These waves are emitted by acoustic sources preferentially generated in absorbing tissues of diagnostic interest. The technique allows visualization of absorbed light distribution in turbid, layered and heterogeneous tissues irradiated by laser pulses in vivo. The laser opto acoustic tomography can be used for the characterization of structure and properties of normal tissue, and for the detection of tissue pathological changes. Three-dimensional images of organs and portions of organs can be obtained.

The photoacoustic imaging method and apparatus described herein can be useful for medical imaging of non-planar light absorbing structures, such as blood vessels, tumors, and internal organs, for imaging of physiological parameters such as oxygen saturation, and for tracking of molecular probes, all in three-dimensions and at high frame rates relative to previously used methods. Embodiments of the systems described herein are suitable for small animal imaging and for clinical use, either as a stand-alone transportable device or integrated with another imaging modality, such as X-ray CT scanner, PET scanner, MRI scanner or a combination thereof. One embodiment of the imaging apparatus can acquire 3-D images with single laser shots at a frame rate of 10 Hz.

The imaging method of the present disclosure is based on the photoacoustic (PA) effect, where a short laser pulse diffusely irradiates a volume of tissue, and is absorbed in the optically absorbing structures therein. These structures undergo a slight but rapid temperature increase, resulting in elastic expansion and generation of an outgoing transient pressure wave. These pressure waves, also called photoacoustic waves, can be detected on the surface of the volume using a wide band ultrasound detector(s). From the surface PA measurements an image of the distribution and relative strength of the PA sources inside the volume can be generated. In general, the larger the solid angle of the surface of detection, the better the reconstruction of the PA sources can be because more viewing angles are captured.

According to one embodiment, the apparatus of the present disclosure uses backward mode illumination where the laser radiation impinges on the volume from the same side as the ultrasound detectors. The detectors are arranged in a sparse array that can be planar or bowl shaped or can be arranged over other surfaces. In an exemplary embodiment of the PA imaging apparatus, the array has a window in the middle for delivery of the laser beam. The subject to be imaged is placed in the area above the optical window and is fully accessible for administration of drugs or anesthetics, monitoring of vitals, or any other necessary handling. Illumination can also be accomplished with multiple laser beams from a multitude of positions and angles around the volume.

SUMMARY OF THE PRESENT DISCLOSURE

According to one embodiment of the present invention, there is provided an apparatus for photoacoustic (PA) imaging of a subject, the apparatus including a holder for supporting the subject, a device for illuminating the subject by means of a beam capable of generating PA waves, and a staring sparse array of transducers for receiving the PA waves and converting these waves to corresponding analog signals. The sparse array has at least three transducers and at least two dimensions. At least some of the transducers are spaced apart from one another in order to provide a wider range of viewing angles of the subject compared to viewing angles achievable with an equivalent number of closely spaced transducers. There is also a supporting structure for mounting the sparse array. The apparatus includes means for acoustically coupling the sparse array to the subject and electronic means for receiving, processing and converting the analog signals to provide corresponding digital signals. A programmed computer system is operatively connected to the electronic means to receive the digital signals and to process these signals by an image reconstruction algorithm to create one or more three dimensional (3-D) images of the subject.

In an exemplary embodiment of this apparatus, the illuminating device is a laser capable of providing a pulsed laser beam.

In an exemplary embodiment, the apparatus includes a separating window structure for separating the subject from the sparse array. This separating structure includes a relatively thin, optically transparent, acoustically transparent window wherein, during use of the apparatus, the illumination from the laser beam passes through the separating structure in order to illuminate the subject and PA waves from the subject pass through the separating structure to the sparse array.

According to another embodiment of the present invention, a method for calibrating an apparatus for PA imaging of a subject is provided. The imaging apparatus includes an array of transducers for receiving PA waves from the subject and converting these waves to corresponding analog signals, a supporting structure for mounting the array, means for acoustically coupling the transducers to the subject, an electronic system for receiving, processing and converting the analog signals to provide digital signals, and a programmed computer system operatively connected to the electronic system to receive and process the digital signals. The calibration method includes providing a point source and means for illuminating the point source by means of a pulse beam, the point source being capable of generating PA waves upon illumination by the beam and being located in the means for acoustically coupling. The point source is raster scanned through a calibration volume so that the source is scanned to and stopped at a plurality of grid points in a predetermined timed manner. Simultaneously, the illuminating means is operated to produce the beam and transmit a pulse of the beam to the point source at each grid point, thereby generating the PA waves from the point source at each of the grid points. The PA waves from each of the grid points are detected by means of each of the transducers and the PA waves are converted to corresponding analog signals. Three dimensional (3-D) characterization maps are then generated from the digital signals by means of the electronic system and the computer system.

In an exemplary form of this method, the illuminating means is a laser capable of generating a pulsed laser beam and the laser beam is transmitted to the point source by an optical fiber.

There is also disclosed an apparatus for calibrating a PA apparatus for PA imaging of a subject. The PA apparatus has an array of transducers for receiving PA waves. The calibrating apparatus includes a laser source for producing a pulsed laser beam, a point source device capable of receiving the pulsed laser beam and generating PA waves at an end of the device, and a mechanism for raster scanning at least a portion of the point source device through a calibration volume so that its end is scanned to and stopped at a plurality of grid points in a predetermined timed manner.

Further features and advantages will become apparent from the following detailed description taken in conjunction with the accompanying drawings.

BRIEF DESCRIPTION OF THE DRAWINGS

FIGS. 42a, 42b and 42c are orthogonal slices illustrating the results of a test where a point source was imaged with backward mode illumination;

FIG. 43 shows four dimensional imaging results from a rotating rod experiment with section (a) showing exemplary 2-D orientations of the rod at four different time points and section (b) showing exemplary 3-D rendering of the rod at one time point;

FIG. 44a shows the imaging results from scanning a point source in the y direction;

FIG. 44b is a 3-D rendering of the same moving target as in FIG. 44a with the axis origin and direction indicated by the arrows.

DETAILED DESCRIPTION OF EXEMPLARY EMBODIMENTS

Figure 1:
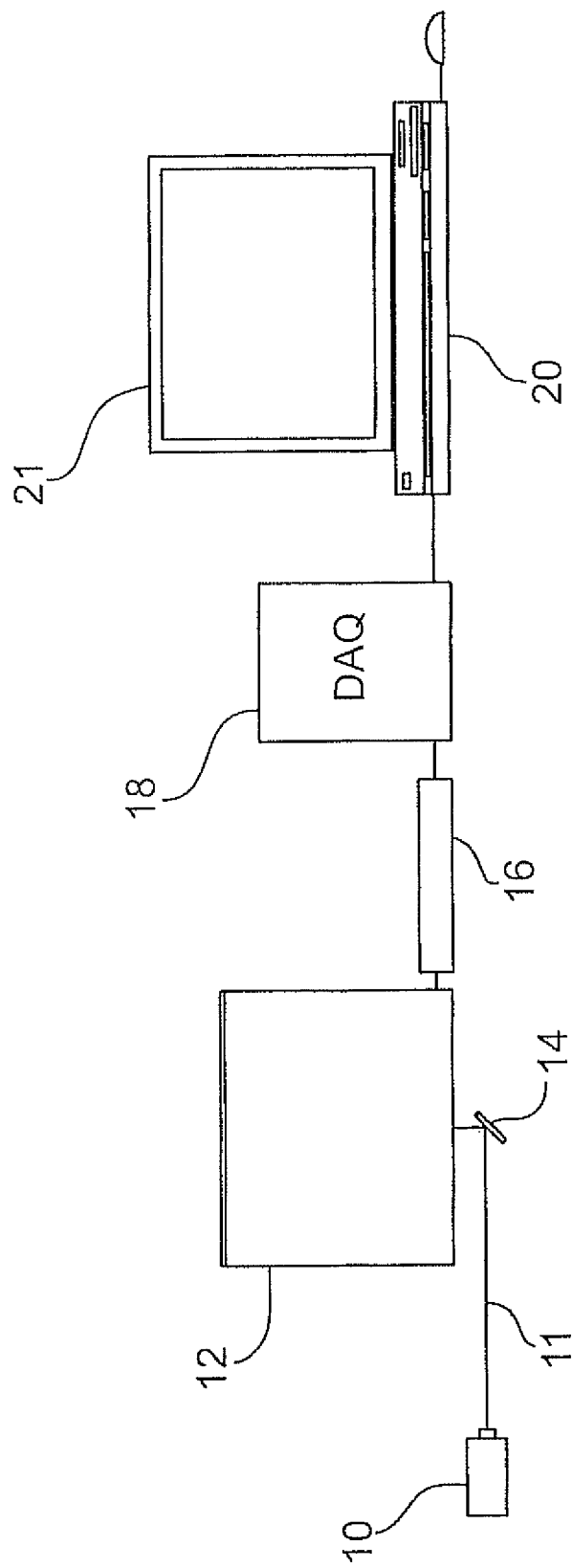
FIG. 1 is a front schematic view of a photoacoustic imaging apparatus in accordance with the present disclosure.
Figure 2:
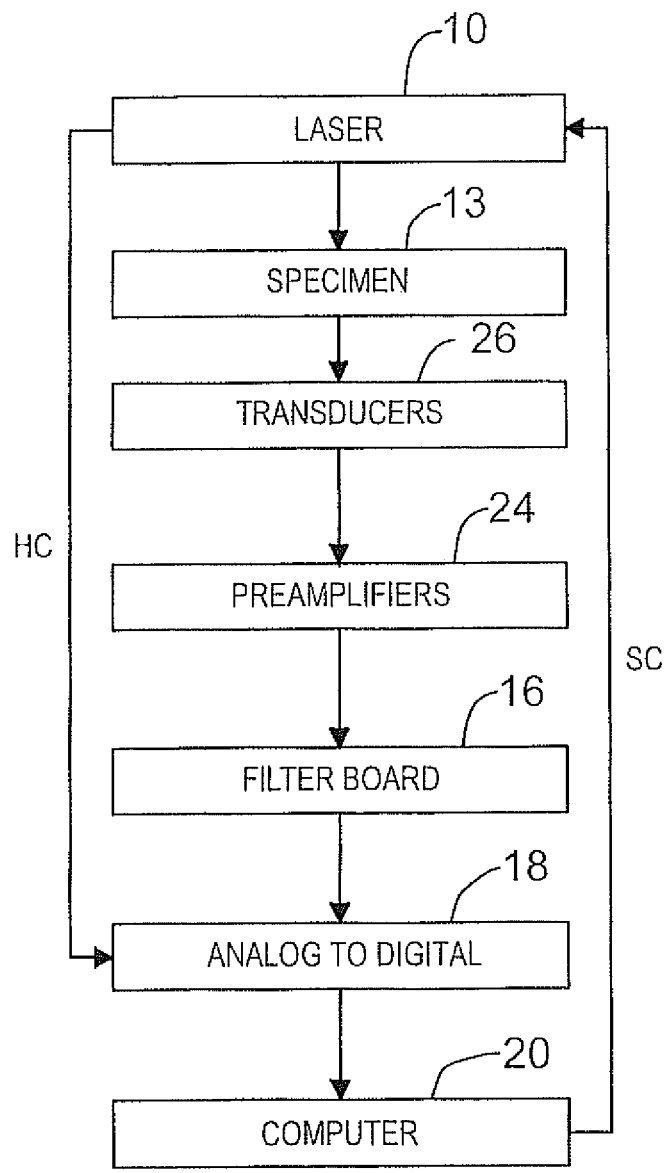
FIG. 2 is a flow chart of the PA imaging system.
Figure 3:
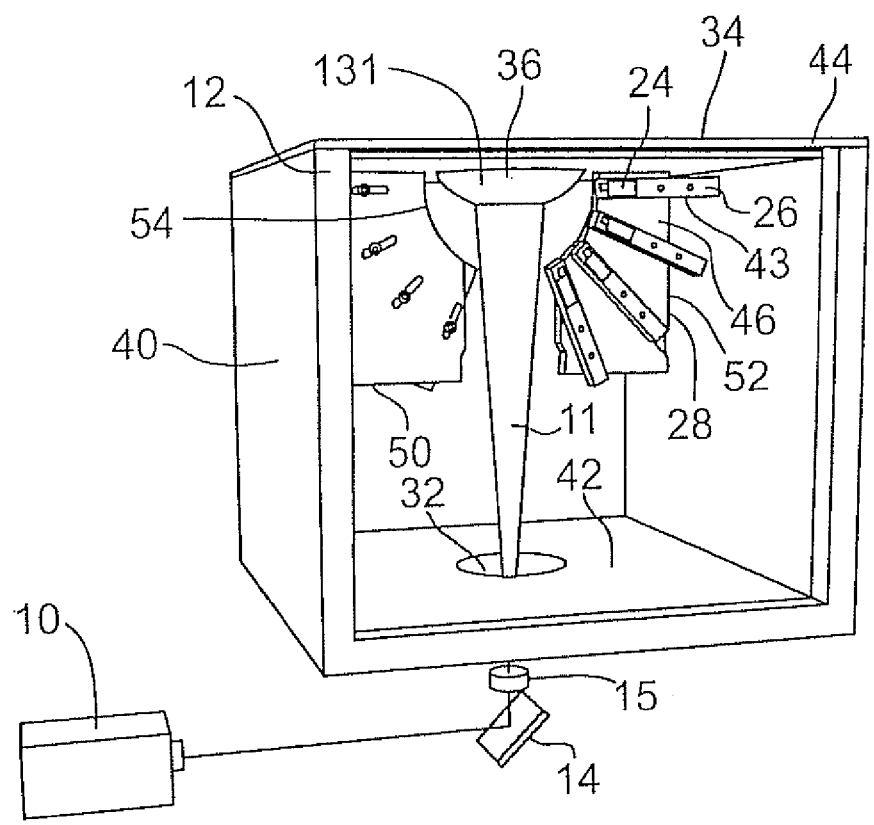
FIG. 3 is a perspective view of a transducer box or tank containing a sparse array of transducers and a laser beam directed into the box from below.
Figure 4:
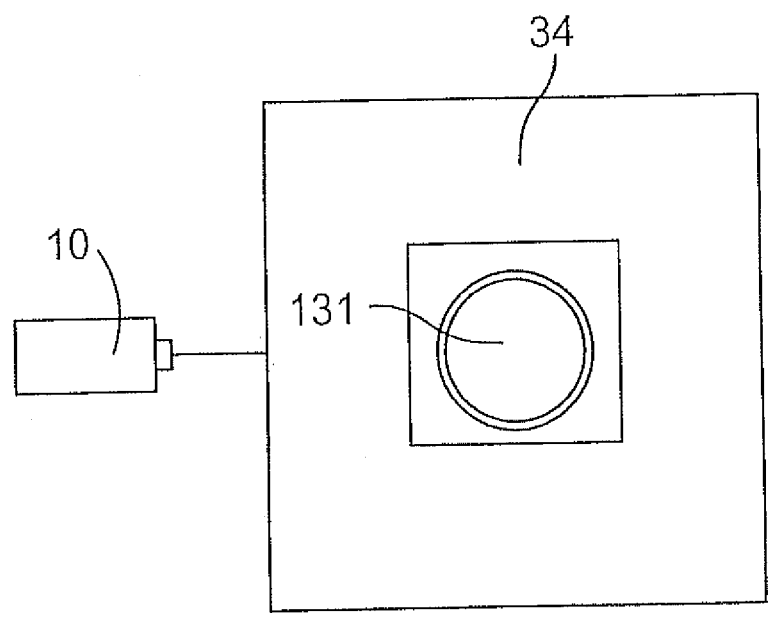
FIG. 4 is a top view of the transducer box of FIG. 3.

A schematic overview of a PA imaging apparatus or system according to the present disclosure is shown in FIG. 1. Laser means in the form of laser 10 is provided for producing a suitable laser beam 11 to illuminate a subject, such as a mouse, for medical or scientific imaging in order to generate a photoacoustic signal. In order to reflect the beam 11 into a transducer box 12, the beam is reflected by a mirror 14 which in the illustrated arrangement slopes at a 45 degree angle to a horizontal plane. The beam is then expanded by a lens 15. The beam then passes through the box as shown in FIG. 3 by passing through a clear bottom window 32 which can be circular as shown. A specimen(s) such as a mouse is positioned on top of the box 12 which can provide a table or support surface at 34 for support of the specimen. A suitably sized hole is provided in the top of the box at 36 for passage of the laser beam. The hole 36 is covered with a suitable transparent material 131 such as Mylar sheet or plastic sheeting such as Cellophane™ which can provide support to the specimen and which also separates the specimen from the interior of the box which is filled with a suitable liquid such as water. Located in the box are a number of transducers 26 which are detectors and are arranged in a sparse array having at least two dimensions. There are at least three transducers in the sparse array of the present disclosure. In the case of the illustrated, bowl-shaped array, the array has three dimensions. Each transducer is capable of receiving and detecting a PA wave which is generated by the illumination of the subject or specimen by the laser beam 11. The PA wave generated by the laser beam is a PA pressure wave which can be converted to an analog PA signal by each transducer 26. The signals produced by the transducer array are sent to a filter card 16 and then to a data acquisition (DAQ) system 18. This system converts the analog signals to digital signals and is capable of capturing in parallel the PA signals from the transducers which are operatively connected through the filter card to the DAQ system. The signals are then sent to a computer 20 and/or cluster of computers which can be a suitable personal computer of sufficient capacity, where the image(s) is reconstructed. The computer 20 as shown is attached to a monitor 21 on which the image is displayed. FIG. 2 is a representative flow chart of this system. As indicated by the arrow SC, the laser is controlled by the software of the computer. FIG. 2 illustrates the control loops involved in the system with box 13 being a specimen to be imaged. A suitable laser system for the above described apparatus is a Q-switched Nd:YAG pump laser with optical parametric oscillator (OPO), Model Vibrant available from Opotek, in California. This laser has a five ns pulse duration at repetition rate of 10 Hz, with energy per pulse >40 mJ and is wavelength tunable between 680 and 950 nm. Thus the laser is capable of producing a laser beam having wavelengths in the visible and near infrared range. The reflecting mirror 14 can have any reflecting surface but in an exemplary embodiment the reflecting surface is made of protected gold. The arrow HC indicates the hardware control between the laser and the DAQ system 18.

The transducer box 12 is completely enclosed on all sides with the front of the box being shown open in FIG. 3 merely for illustration purposes. Although it is possible to make the box from a variety of waterproof materials, in an exemplary version of the box, it is made of blackened Plexiglas™. The illustrated box has four vertical side walls 40, a bottom 42 and a removable top 44. The bottom window 32 is formed centrally in the bottom 42. The transducer array 28 can be mounted as shown to the bottom side of the top 44. In the alternative, the transducer arrangement can be mounted to the bottom of the box. The box is constructed as a leakproof tank so that it is capable of holding liquid such as water or distilled water. Although the illustrated box 12 is six sided and rectangular when viewed from each side, other shapes are possible for carrying out the method of PA imaging according to the present disclosure. For example, in one embodiment, the transducer box or tank (also referred to herein as "tank means") is a relatively small regular cylinder with a diameter of about three inches.

The transparent material forming the optical acoustic window 131 should be thin, in the order of 10-15 microns thick. The optical window should also be strong enough to support the subject placed over the window. Another material that can be used to achieve the required acoustic coupling between the sample or subject to be imaged and the detectors is a small amount of water suitably contained above the optical window. In other words, the subject can lie in the region of the optical window in the small pool of water. A flexible plastic sheet such as Cellophane™ can, if necessary, be used to contain the water.

FIG. 3 illustrates one form of transducer array indicated generally at 46 comprising four separate array sections, each of which has a transducer holding plate or holder 28. This array can be considered generally as "bowl shaped". This plate has straight top edge, a bottom edge 50, and a straight side edge 52. One corner of the plate is cut away so as to form a curved side edge 54 along which the transducer elements 26 are distributed as shown. In the illustrated version, there are four of these elements mounted on each holder 28 and they are separated by gaps along the curved edge 54. Each transducer element can be detachably connected to the holder by a suitable fastener such as a screw. In this embodiment, each transducer element comprises a PVDF sensing film glued to a transducer body which is long enough to carry reverberations away from the interval of signal acquisition. A preamplifier card at 24 is attached to each transducer element 26 at close proximity to the sensing film to minimize noise pick up. The signal acquired at the sensing element is amplified at the pre-amplifier card 24. The analog signals from the preamplifier are sent to the filter card 16. This filter card takes the analog signals from the pre-amplifier cards 24 and subjects them to a band pass filtering process which filters out signal components that are below a certain frequency and all signal components that are above a certain frequency. The filter card then amplifies the analog signals and sends them to the data acquisition system 18. Note that the signals from the transducer elements of the array need to be acquired simultaneously by the system in order to generate a true representation of the PA sources. In order to acquire the multiple analog signals, a multi-channel analog-to-digital convert system is required. The holder 28 can be formed with slots or grooves in which are mounted the modular transducers 26 with the pressure sensitive end of each transducer facing a focal point. Each of the four transducers can be adjustably mounted by means of another slot extending through the holder 28 and an adjustment screw that extends through this slot into the transducer body. In this way, the pressure sensitive end can be moved closer to or further away from the focal point. It will be understood that pressure waves created by the laser beam with frequency components over the range of 2 KHz to 25 MHz appear at a front surface 27 of the transducer which is composed of the piezoelectric material.

Figure 19:
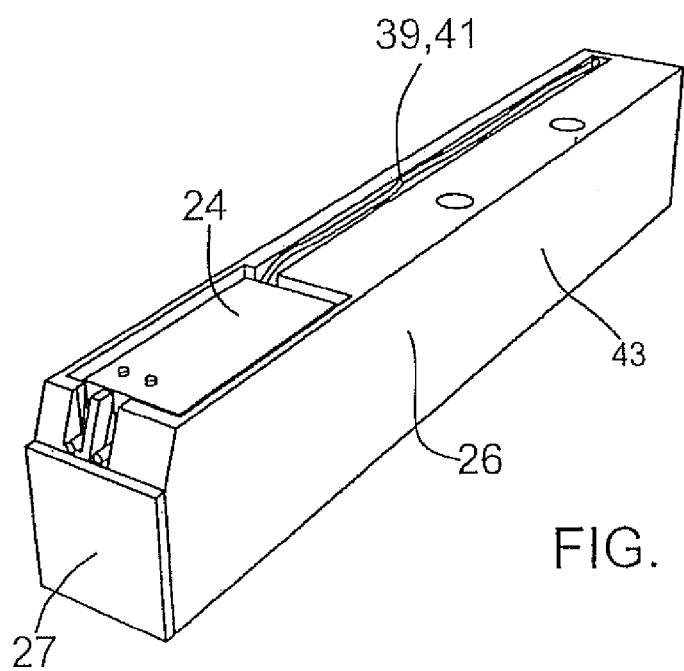
FIG. 19 is a perspective view of the transducer used in the array of FIG. 3.

The ultrasound pressure waves received from the specimen are converted to a voltage difference between the front surface 27 and a back surface of the piezoelectric material. The front surface of the material is connected to a negative input of the preamplifier 24 (see FIG. 19). The back surface of the piezoelectric material is connected to a positive input of the preamplifier. The preamplifier is supplied with a driving voltage through a power cable 39 and the amplified signal from the preamplifier is connected to the DAQ system by way of a signal cable 41. The elongate body 43 of the transducer element is formed by milling a material, i.e. clear acrylic, that has a speed of sound closely matched to the piezoelectric material.

In order to represent the analog signals digitally with sufficient resolution the converter for the PA imaging system has to have at least 6 bit resolution (and preferably 12 bit resolution) and it has to operate at high frequency (i.e. 5 MHz or greater, preferably 50 MHz or more) in order to resolve the temporal signal and enable sufficient spatial resolution in the reconstructed image. The number of channels required in the data acquisition system 18 is equal to the number of elements in the transducer array, plus one channel for the light sensing element that is used to monitor the laser 10 energy. The transfer of the digital signal from the data acquisition system 18 to the computer 20 can be accomplished several ways, for example, by USB, parallel port, high speed data bus, etc.

In an exemplary version of a dedicated data acquisition (DAQ) system capable of acquiring multiple signals in parallel with high temporal resolution and wide dynamic range, the system comprised a chassis holding multiple boards, each board having eight analog to digital converter channels. Each channel has a sampling rate of 50 MHz, a resolution of 14 bits (12 $\mu$V resolution with input range of 200 mV), and its own memory where the digital signal is stored after conversion. The digital signals were transferred from the DAQ memory to the computer via a communication bus (RS232 or USB). Data transfer was facilitated by custom control software (LabView, National Instruments) that also served to control and synchronize the laser, a robotic gantry and the DAQ system 18.

It will be appreciated that the apparatus and system of the present disclosure relies on a staring transducer array which can provide the advantages of inherent speed and sample accessibility compared to known prior art systems. With a sparse transducer array, the detectors or transducer elements are spaced out to cover a relatively large area but with a low packing ratio instead of being as close together as possible. The spread of the transducer elements over a large area is desirable to provide a wide range of viewing angles of the volume to be imaged, which improves the boundary reconstruction of PA objects in the field of view. The geometry of the exemplary sparse array is annular to accommodate backward mode illumination of the object through the center of the annulus, which results in the advantage of easy object placement and accessibility.

With an exemplary system of the present disclosure, the object to be imaged is readily accessible. The object can be simply placed on top of and held on a flat, supporting surface having a transparent aperture for the laser beam. The object can be fully accessible from the top and the sides and can, for example, be held down by suitable tape or straps and is able to breathe normally. Drugs can be administered to the subject, for example, by means of a hypodermic needle. The region to be examined can be placed directly above the aperture and this region is maintained in acoustic contact with the detector array. Good acoustic contact can be maintained between the subject and the transparent support material over the aperture by means of an ultrasonic gel, for example. The PA signals are acquired once for all detectors in the array and sent to the computer 20 via the DAQ system 18. Alternatively, improved PA signals can be obtained by averaging results from multiple laser pulses. This PA imaging system can be used to collect one 3-D image for each laser pulse (or specified number of laser pulses) which will enable one to capture a sequence of 3-D images which can provide a 3-D movie of the subject.

Figure 5:
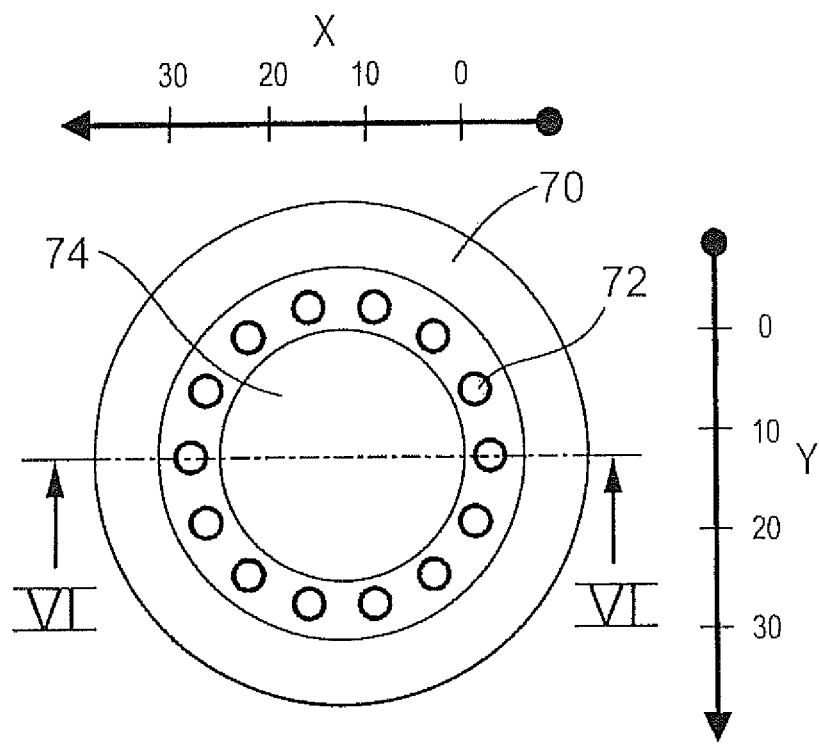
FIG. 5 is the schematic top view of another sparse array with the detectors arranged on an annular holder.
Figure 6:
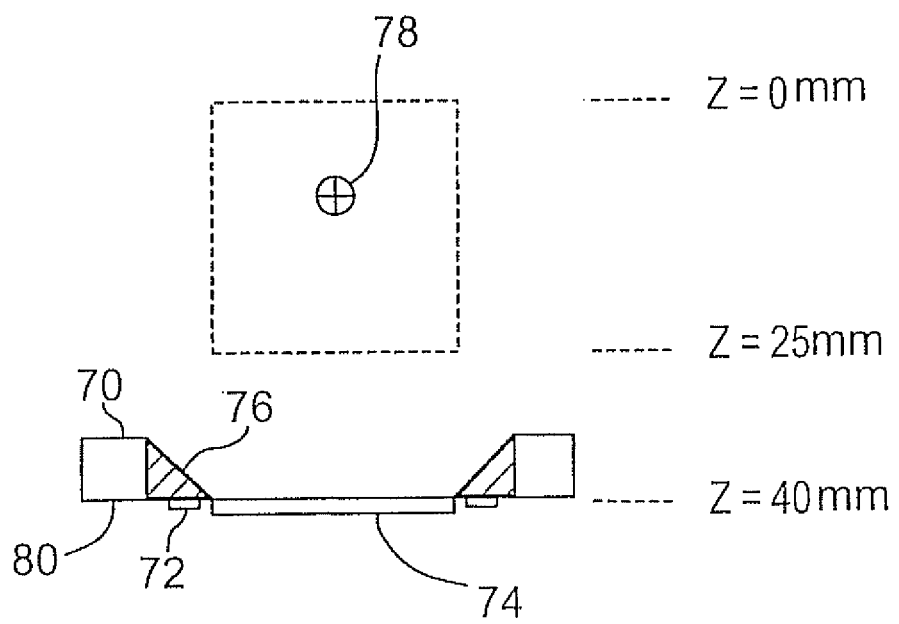
FIG. 6 is a cross-sectional view of the detector array of FIG. 5, this view being taken along the line VI-VI of FIG. 5.

FIGS. 5 and 6 illustrate schematically another embodiment of a sparse annular transducer array including an annular plastic holder 70 for the transducers. As illustrated, the array has fourteen PVDF film detectors 72 mounted on a bottom surface of the holder. In a particular embodiment, these detectors or transducers had a diameter of 3 mm each and were arranged at a diameter of 30 mm around the annular holder 70. The detectors were made of 110 $\mu$m thick metallized polyvinylidene fluoride (PVDF) film (P/N3-1003702-4 from Measurement Specialties Inc. of Virginia, USA). An optical window 74 is mounted over the circular central hole of the holder allowing for laser transmission through this central hole. A transparent material that can be used for the optical window is glass or quartz which is sufficiently strong to provide support for the subject, such as a mouse in this area. An annular delay line has a wedged area (cross-hatched) 76 which is located directly on top of the detectors and this delay line produces a refraction of the acoustic waves arriving at the detectors so that an effective focal zone is created above the center of the array which, in a particular embodiment was at a height of 30 mm. This focal zone is indicated by the crosshair 78.

Although the number of transducers in any sparse array according to the present disclosure can vary with each PA imaging system, generally the number of transducers will range between 3 and 128, a number far fewer than that employed in the dense arrays of previously known 2-D array systems. However it is also possible to construct a sparse array having up to 256 transducers provided the connected electronics system and the computer system are equipped and programmed to handle this many transducers. Despite the limited number of detectors used in the present systems, with these systems it is possible to create a 3-D image from the limited data set with good contrast and reduced artifacts. Also, the present imaging system is fast and is able to produce 3-D images with a single laser shot, meaning that the information is acquired on a time scale of nanoseconds. Because of this, for example, it is not necessary that the subject being imaged be secured in such a manner to ensure that it remains perfectly still during the imaging process. For real time imaging using the present system, the frame rate is limited by the laser repetition rate, data transfer time to the PC and image reconstruction calculations. With current components, the limit of the system is around 10 3-D frames per second, but with faster lasers 20 to 2000 frames per second are achievable. The theoretical limit is 10,000 frames per second for an object within 15 cm of the transducer array.

With further reference to FIG. 6, the slope or angle of the wedge formed by the annular plastic holder 70 is significant and is determined in a known manner by means of Snell's law, taking into account the refractive index between water (assuming water is used to provide the acoustic coupling) and the plastic used to provide the wedge surface, bearing in mind that the holder 70 is made from solid plastic. The purpose of the wedge shape of the holder is to focus the detectors so that they provide overlapping coverage in an elevated area. The annular plastic holder 70 can be coated with an optically reflective material such as gold to prevent loading of the transducer elements by the laser beam. In one version of this holder, it is made of clear acrylic plastic but polycarbonate plastic can also be used and it is not necessary for the plastic material to be clear. In the case of an acrylic holder, the angle of the wedge is about 55 to 60 degrees to the horizontal plane defined by the side 80. The precise angle of the wedge is not critical because a slightly different angle simply changes the location of the focus point.

As indicated, an exemplary material from which to make the detectors or transducer is PVDF film which is a very good material for sensing ultrasound waves and has a larger bandwidth than regular commercial piezoelectric materials. However, other known piezoelectric materials can be used for this purpose as well as other known acoustic sensors, such as Panametrics NDT V382-SU.

Figure 7:
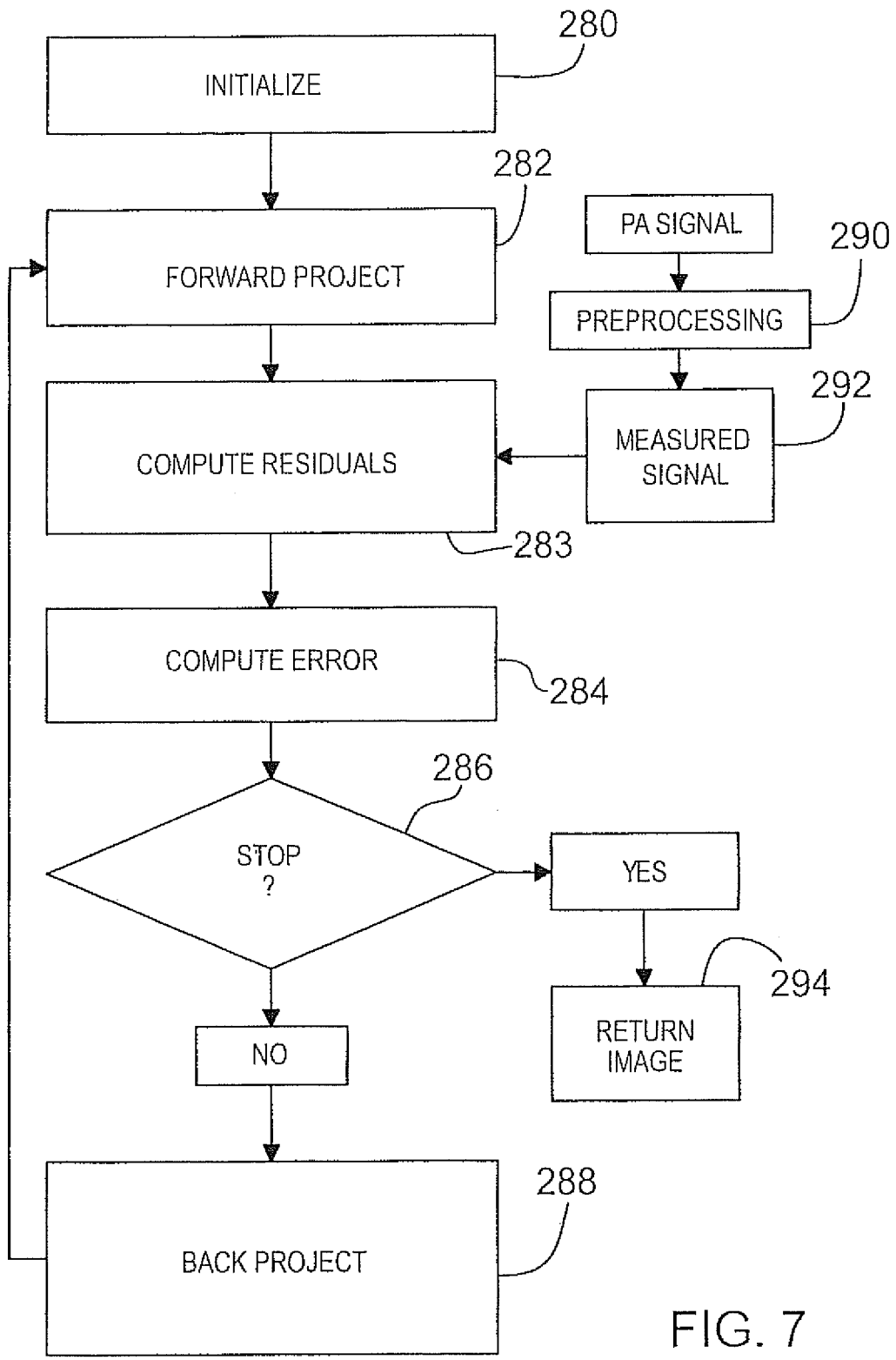
FIG. 7 is a flow chart of an image reconstruction algorithm for creating a PA image from PA signals.

FIG. 7 provides a flow chart of an image reconstruction algorithm (IRA) for creating a PA image from PA signals. At the first step 280 the reconstructed image estimate (RIE) is initialized to contain only values of zero (0). In the second step 282, the reconstructed image estimate is forward projected to obtain a velocity potential estimate (VPE). The next step 283 computes a differential velocity potential estimate by subtracting the VPE from the measured velocity potential (MVP). The steps to obtain the MVP are shown on the right side of the flow chart. The PA signal generated at each transducer is preprocessed at 290 by the electronics system which provides offset correction, rectification and filtering in order to provide the MVP to the computer system. It is also possible for the computer to compute the MVP from the digital PA signal.

At step 284, the computer system 20 calculates the mean squared error (MSE) of the differential velocity potential (VP) estimate. In the next step 286, the computer determines if this MSE meets the stopping criteria stored in the computer program. If the answer is "Yes", then the algorithm is finished. If the answer is "No" the algorithm goes to step 288 where the differential VP estimate is back projected to obtain a differential image estimate and the RIE is then updated as the previous RIE plus the differential with all resultant negative image values set to zero (0).

Calibration of the Transducer Array

Figure 9:
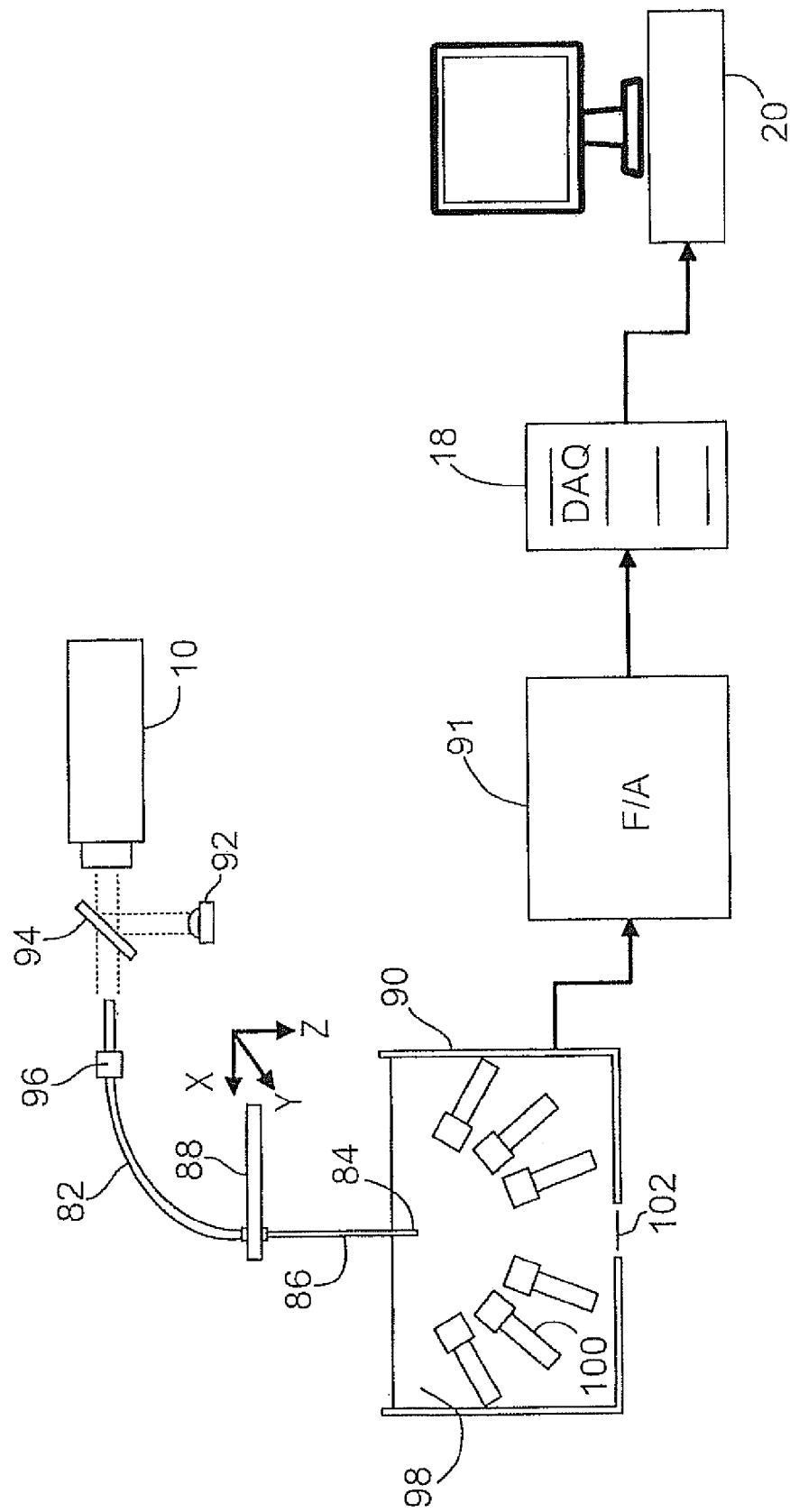
FIG. 9 is a schematic front view similar to FIG. 8 but showing a system for providing a spatial calibration scan using a PA point source.

In order to account for the response profile of each transducer in a PA imaging system according to the present invention and for the overall response profile of the array, a spatial calibration scan is performed where a PA point source is raster scanned through the image volume and 3-D characterization maps are generated. One system employed for this calibration scan is illustrated in FIG. 9. The point source is constructed from an optical fiber 82 whose tip at 84 is polished and coated with black paint. The fiber has a core of 400 microns (μm) diameter. The optical fiber extends through a stainless steel hollow needle 86. The needle can also be made of aluminum, aluminum alloy or some other suitable rigid material that is not affected by the water in the tank. Both the end of the optical fiber and the end of the needle are polished at the same time and coated with the aforementioned black paint. Instead of this paint, it is also possible to use a suitable opaque material such as carbon or tungsten. It will be understood that the laser beam from the laser 10 that travels through the optical fiber is absorbed at the black coating and this produces a photoacoustic wave at the tip of the needle.

In order to use the fiber-tip system of FIG. 9 as described above, the angular dependence of the acoustic field generated by the coated fiber-tip was measured by mounting the fiber-tip on a rotating holder so that the axis of rotation was at the tip. As the holder was tilted, the coated fiber turned away from the transducer below it but its tip remained in the same X-Y position directly above the transducer. The results indicated that the field was constant up to angles of 20 degrees and was reduced by 75% at an angle of 30 degrees. This result is not what one would expect from a true point source where the angular dependence is flat for a much wider range. The difference was apparently due to the flat surface of the black coating which limited the acoustic propagation in large angles. With this system measurements done at source-detector angles smaller than 20 degrees are valid and larger angles can be corrected for.

A robotic scanning gantry shown schematically at 88 and constructed from three linear slides (available from Zaber Technologies) arranged in a xyz configuration is used to scan the PA source, that is the point of the needle. In an exemplary embodiment the gantry 88 is equipped with an articulating robot arm which allows rotation of the point source in combination with translation in x, y, and z. Examples of suitable and commercially available robot arms include model G6-65X and model Pro Six PS3 from Epson Robots. By means of this gantry, it is possible to calibrate the array at a multitude of grid points within the water filled tank 90 which can have a cylindrical shape. In other words, the PA point source provided at the end of the optical fiber is raster scanned through a grid of points in the imaging volume. For each grid point, the PA wave is picked up by each transducer at a slightly different angle and delay time. For each grid point, the distances from each transducer to each voxel are calculated from the time-of-flight information, the sensitivity of the transducers is calculated from the relative amplitude, and the temporal width of the PA signal is recorded. The coverage map that is produced is a global descriptor of how many detectors provide sufficient PA signal above background noise at each voxel in the imaging volume.

At each grid point of the scan, the probe or needle 86 was motionless and the laser was fired through the fiber 82 resulting in a pressure transient generated at the coated tip. Each transducer element produced an analog voltage proportional to the pressure profile which was amplified and filtered by means of a standard filter/amplifier unit 91 and sent to the DAQ system 18. For each laser pulse, part of the laser beam was directed towards a photo-diode 92 and recorded synchronously with the DAQ system to monitor fluctuations in laser power. Although the system shown in FIG. 9 employs a semi-transparent mirror 94 capable of reflecting a portion of the laser beam to the photo-diode, in another PA imaging system, the optical fiber 82 is split so that a portion of the laser beam is transmitted to the photo-diode 92. The photo-diode can be of standard construction, is a well known component in laser monitoring systems, and has the advantage of being fast so that it is capable of sensing a rapid fluctuation, The receiving end of the optical cable is mounted by means of a standard head 96 which holds this end securely in position. As indicated, the scan is performed in water 98 which can be distilled water and this water is used for acoustic coupling between the source and the transducer array 100. In one particular scan, the volume scanned was a 25×25×25 mm$^3$, extending from (x,y,z)=(0,0,0) to (x,y,z)=(25,25,25). The volume was chosen to cover the area of the optical window 102 in the xy plane and to cover the focal zone of the annular array in the z-direction. The acquisition points were spaced 5 mm apart in the x-, y-, and z-directions for a total of 216 points that spanned the volume. The datasets acquired from the array transducers at each grid point were fed into the analysis software, where the location, width and strength of each PA peak was detected, and the effects of laser power variation and acoustic spherical divergence were taken into account. The software generated a sensitivity map for the transducer array that depicted the relative strength of the PA signal detected by each element at each grid point. The sensitivity map was used as a weighting function by the image reconstruction algorithm.

A coverage map was also generated by the analysis software which was qualitative in nature. For each voxel, the coverage map depicted the number of elements in the array that received signals above background noise. Visualization of the regions of maximum coverage gave an indication of where the best imaging quality was to be expected since for voxels where coverage was good, the reconstruction algorithm is able to incorporate data from a multitude of angles.

Figure 8:
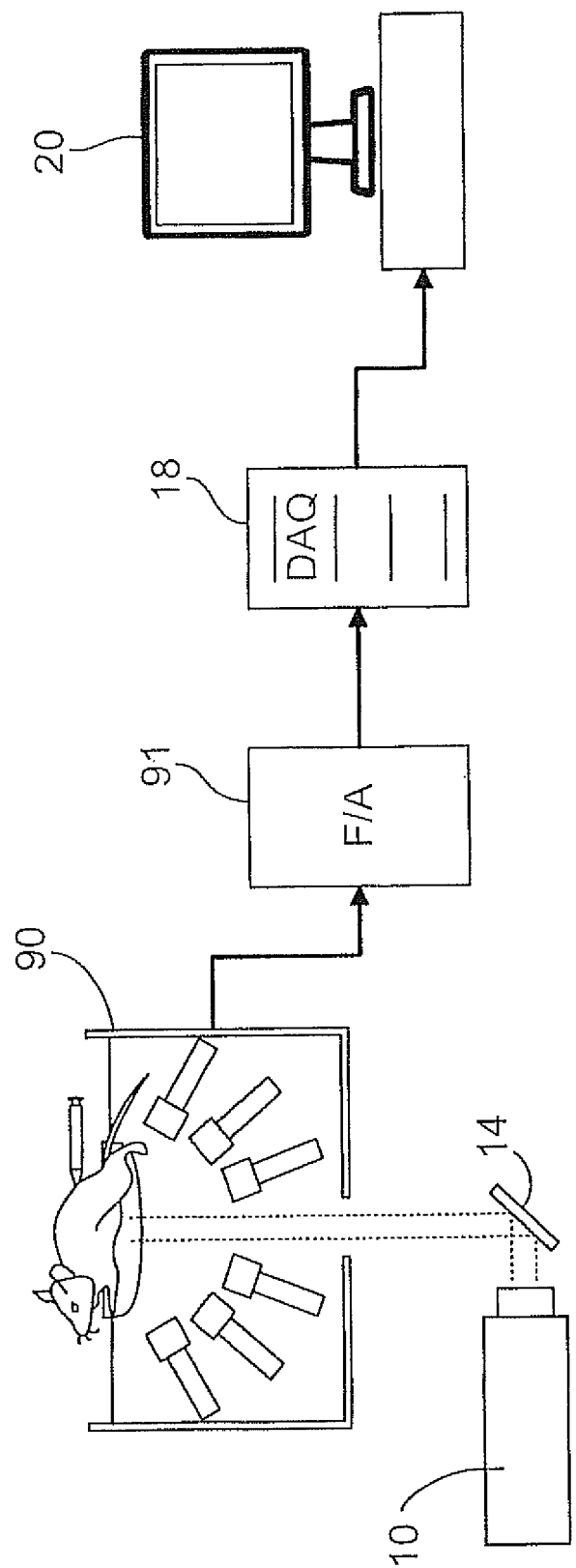
FIG. 8 is a schematic front view of a photoacoustic imaging apparatus similar to FIG. 1 but showing a cross-section of a tank in which a sparse array of transducers is mounted.

Although one can use for this sensitivity mapping the above described transducers (shown in FIG. 3), an exemplary array of transducers shown in FIGS. 8 and 9 consists of fifteen commercially available ultrasound transducers such as Model V304, 1" diameter, 2.25 MHz immersion transducer available from Panametrics-NDT of Waltham, Mass. These detectors can be mounted on five custom-built curved holders, each holder supporting three transducers at elevation angles of 22.5 degrees, 45 degrees and 67.5 degrees. The five holders are arranged about a horizontal circle with azimuthal separation of 72 degrees. Tests have shown that this transducer arrangement in which the detectors are distributed evenly over multiple elevation angles leads to greater symmetry in the spatial resolution across all three coordinate directions.

Figure 33:
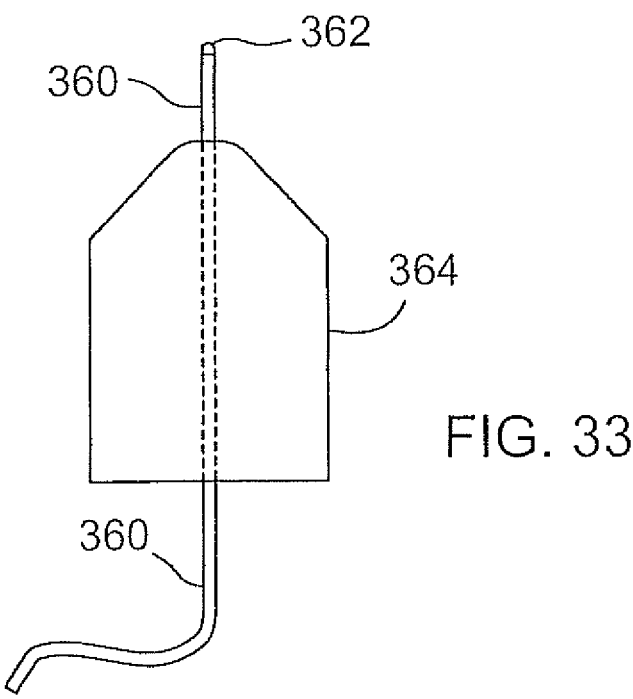
FIG. 33 is a schematic diagram of one embodiment of a point source that can be used for a calibration scan.

As indicated above, the coated flat tip for a point source of the PA waves has an emission profile which is limited in the elevation angular range. An alternative point source which has a more omni-directional emission profile can be made using a 400 μm core optical fiber exposed at one end, polished to a near-hemispherical shape and coated with black paint. Such a point source is described schematically in FIG. 33. The source is constructed from a fiber optic cable 360, whose core size can be 400 μm in diameter, with its tip coated with a opaque material 362 and with the fiber optic cable and coated tip mounted inside a rigid holder 364. The tip of the fiber optic cable is polished into a substantially hemispherical shape so as to improve the intensity of PA waves produced off the axis of the fiber direction by the tip when illuminated by a pulsed laser beam either through the fiber 360 or from outside the fiber. This PA source produces a substantially omni-directional PA wave profile. In a calibration scan using this point source, the centre of the calibration-scan volume was chosen to align with the intersection of the detectors' lines of sight and the volume size was 25×25×25 mm$^3$.

Figure 10:
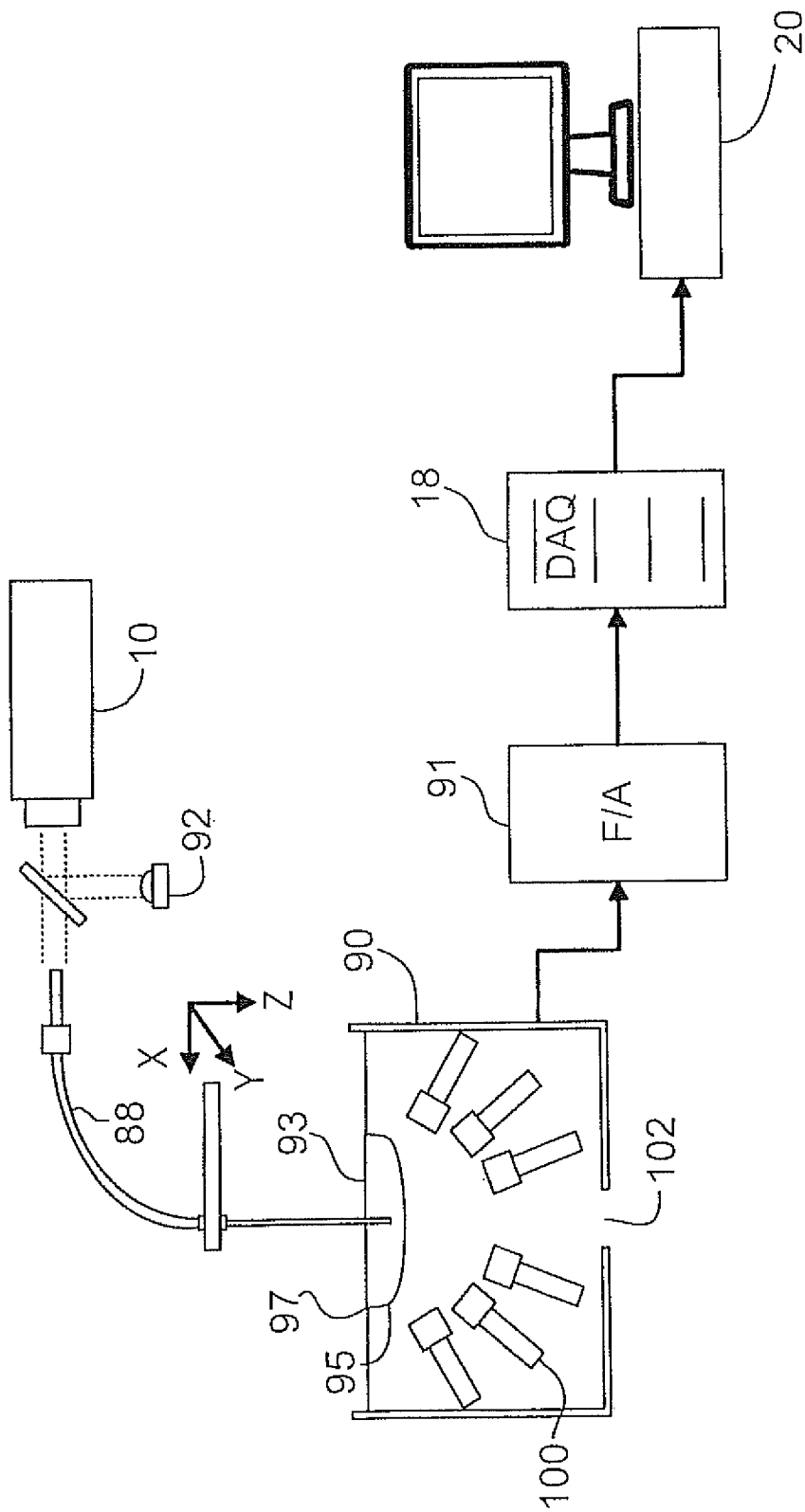
FIG. 10 is a schematic view similar to FIG. 9 but having a PA point source in the form of an optical fiber illuminating a dye filled compartment.

The scanning calibration system shown in FIG. 10 is similar to that described above and shown in FIG. 9 except for the point source 93 which provides a different optically absorbing medium. In this version, instead of an opaque coating at the end of the fiber 82, there is a small pool or body of opaque liquid such as ink or Indian ink which can absorb the laser light. The liquid is held in a bowl 95 which is acoustically transparent and has a top edge 97 above the level of the water in the tank. The bowl can be supported in the tank by suitable support brackets (not shown). With this system the concentration of the liquid in the bowl can be adjusted in order to adjust the size of the PA source.

To validate the accuracy of the 3-D image reconstruction, a 3-D phantom that had a distribution of PA sources with known spatial locations was developed. Instead of building a physical phantom of small absorbing objects, a composite of the PA signals collected during the sensitivity scan was used to build up a synthetic phantom of point absorbers. This approach has two advantages: (i) the position of each absorber is accurately known and referenced to the same coordinate system as the imaging volume, and (ii) the PA signal intensity is constant regardless of position, since the source is illuminated through the optical fiber and the signals are corrected for variations in laser pulse energy. Time domain signals representative of a distribution of point sources are generated based on the principle of linear superposition by separately summing the time-domain signals measured from each detector element when the source is at each location in the distribution. This approach provides a means to generate a variety of synthetic phantoms with user-defined distributions of point absorbers. Although the synthetic sources are accurately localized and uniform in intensity and therefore well suited as test objects for the 3-D PA imaging system, they do not represent a real imaging condition with external illumination and simultaneous detection of multiple point absorbers. To test 3-D PA imaging on a real point absorber with external illumination, the coated fiber tip is used as the point absorber and illumination is done by backward mode through the laser access window instead of through the fiber directly. All phantom experiments were carried out with distilled water as the acoustic coupling medium.

The photo-diode 92, which is a form of photo detector, is also used in this system to monitor fluctuations in the laser power. In order to direct part of the beam to the photo-diode, either a semi-transparent mirror can be used or a bifurcated optical fiber cable which directs part of the beam to the photo-diode. Other forms of photo detectors that can be used to measure the illumination include photomultiplier tubes and cameras.

Figure 11:
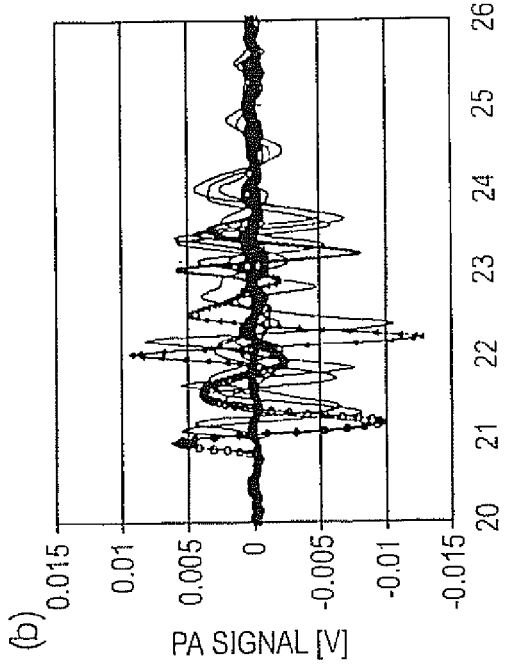
FIG. 11 is a graph of PA signal [V] versus Time illustrating typical PA signals acquired at one calibration scan point.
Figure 12:
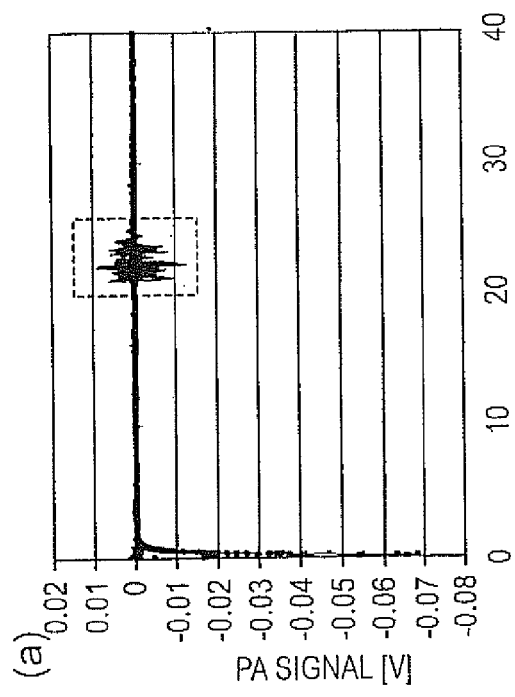
FIG. 12 is another graph of PA signal [V] versus Time providing a close-up view of the PA signals of FIG. 11.
Figure 13:
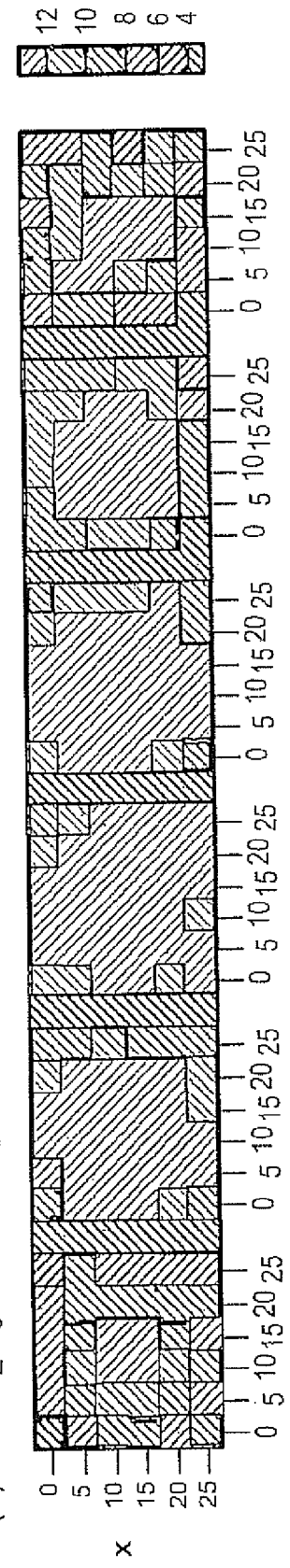
FIG. 13 is a representation of a calculated coverage map illustrating the coverage at six locations along the Z-axis.

FIG. 11 and FIG. 12 show typical PA signals acquired at one of the calibration scan points. FIG. 13 represents the calculated coverage map. In the test conducted, the coverage peaked at the center of each xy plane, as expected from symmetry, but there was also a focusing effect along the z-axis. The largest lateral extent was observed in the plane z=10 mm, and the coverage diminished toward both higher and lower z-values. The coverage distribution in 3-D, hence, took a form similar to an ellipsoid. The center of the ellipsoid was located directly above the array center and at a distance of 30 mm from the plane of detection. Its short axis, oriented laterally, and long axis, oriented along the z-axis, were 15 and 30 mm long, respectively.

Figure 14:
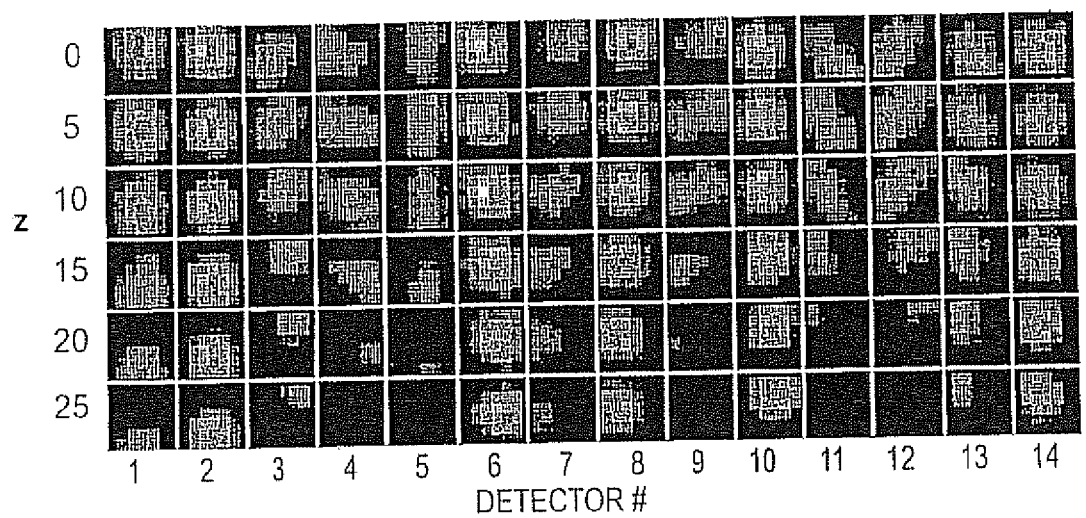
FIGS. 14 to 17 are illustrations of characterization maps that are calculated from calibration of the sparse transducer array.

FIGS. 14 to 17 show the calculated characterization maps. FIG. 14 describes the relative sensitivity of each array element to each voxel in the volume under investigation. The map displays the xy distribution for each z-plane (map rows) and for each detector element (map columns). In the z-direction, the combined effect of the geometry of the array arrangement and the response profile of each transducer can be appreciated: Starting at the bottom row (i.e. the highest z value and the xy plane closest to the transducers) the most compact distribution is observed. Moving away from the transducers, the distribution becomes extended in the xy plane. The location of the centre of the distribution, however, also shifts away from the transducer location for increasing distances from the array. For example, at z=25 mm the distribution for detector #7 peaks at the bottom left corner, which is closest to the detector location; at z=0 mm it peaks on the opposite side, at the top right corner.

Figure 15:
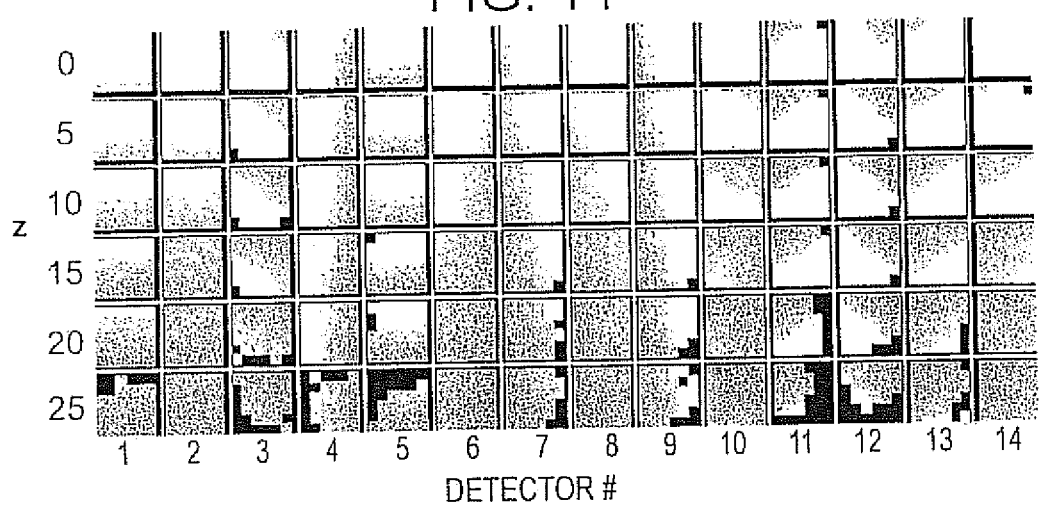
Figure 16:
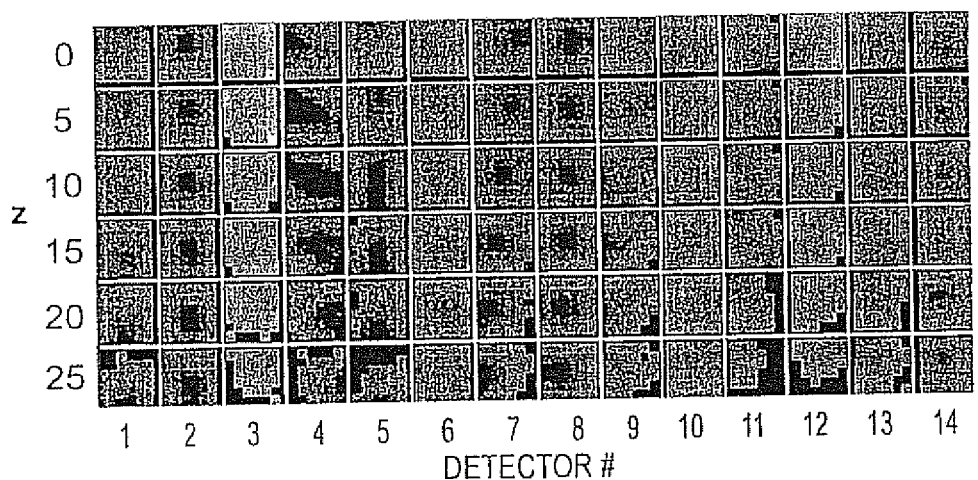
Figure 17:
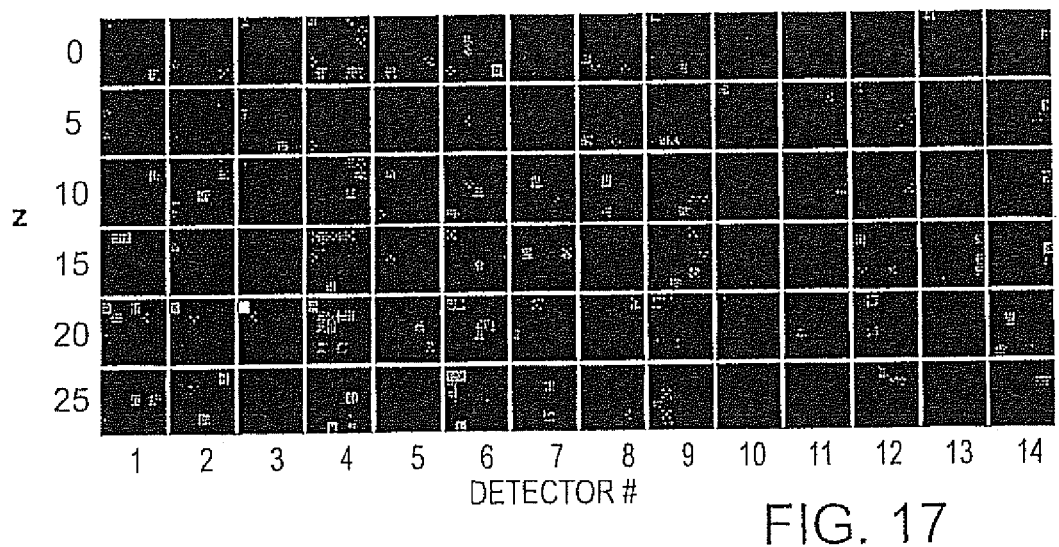

FIG. 15 describes the perceived distance, calculated from the measured arrival time of the PA signal peak, from each array element to each grid point in the calibration scan. The perceived distance can be used in the image reconstruction algorithm for calculations involved in the forward and back-projection processes. The perceived distances are not necessarily equal to the geometrical distances calculated from the coordinates of the transducers and of the calibration grid points. FIG. 16 shows the distance error, defined as the difference between the perceived and geometrical distances. It can be seen that the distance error becomes larger at points on the edge of the volume, where the elevation angle relative to the line-of-sight of the transducers is highest. Experiments have shown that the use of perceived distance in the image reconstruction algorithm, rather than geometrical distance, yielded less image artifacts at the edge of the imaging volume. FIG. 17 describes the full width half-maximum (FWHM) of the PA signal peaks, measured by each array transducer at each grid point of the calibration scan. The FWHM is larger at grid points where the elevation angle relative to the line-of-sight of the transducers is higher, due to the integrating nature of the transducers used. This effect is expected to be more pronounced for larger-area transducers. The maps in FIGS. 15-17 are displayed in the same format as in FIG. 14, where the map displays the xy distribution for each z-plane (map rows) and for each detector element (map columns).

The sensitivity of a transducer is maximal directly along its line-of-sight axis, and drops off in all directions as a function of distance. This can be translated into an angular response profile, as presented in FIG. 18 for three detectors. The sensitivity measured at x-y coordinates far from the axis represents the limiting sensitivity that could be measured with this system. This "Noise Equivalent Sensitivity" originates from spurious peaks in the time series signals, which confound the peak detecting algorithm when they are of strength similar to the true PA peak. Hence the limit to peak detection and to sensitivity measurement is governed by the spurious, rather than the rms noise of this system. The results of the angular response profile (FIG. 18), obtained from calibration of the specific array depicted in FIG. 5, where the FWHM comes to ~10° suggest that the center frequency of the transducers is ~1.5 MHz and hence their center wavelength in water is ~1 mm.

Figure 18:
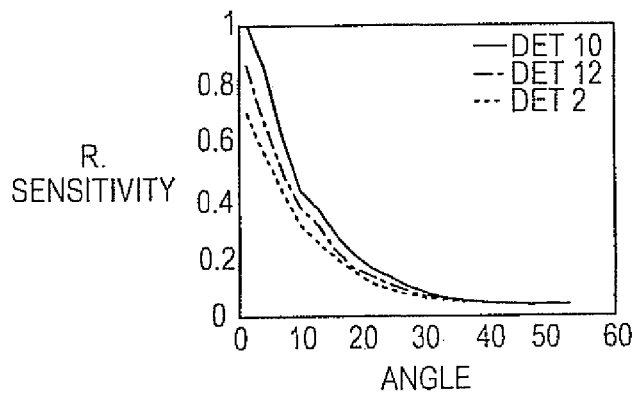
FIG. 18 is a graph of Relative Sensitivity versus Angle (in degrees) from the normal to the transducer surface showing the angular response profile for a few transducer elements (Det 2, Det 10, Det 12)

The angular response for each transducer was calculated by binning the sensitivity values from all voxels by the angles they subtend to the transducer's line of sight, and then averaging the sensitivities within each bin. The number of bins used was 20, and the angle range was 0-35° at a height of 30 mm. Some typical results are shown in FIG. 18 for a height of 30 mm. The variation in sensitivity between transducers is visible, but the shape of the response profile is similar. The FWHM of the angular profile corresponds to the divergence half-angle of the detector's field. The mean value, averaged over all transducers, was calculated to be 9.1°±0.8° at height of 30 mm.

From mapping of highest sensitivity two practical conclusions can be drawn—(i) one should plug into the reconstruction algorithm a scaling factor $0<\eta_i<1$ that takes into account the different peak sensitivity of each element. This factor comes into play twice: when back projecting the signal of element i into the volume, an enhancement multiplier of $1/\eta_i$ needs to be used, and when forward calculating the contribution from each voxel at element i, the signal needs to be attenuated by $\eta_i$.—(ii) the sensitivity map has its peaks close to the transducers' location (on a ring) while the coverage is maximal in the center of the ring. This has consequences for the design of the transducer array.

The sensitivity distribution, and especially the angular response profile, needs to be plugged into the reconstruction algorithm as well. The forward projected signal at the detectors should be attenuated for contributions from large angle voxels. The signal back-projected into such voxels, however, should be enhanced and one should avoid divergence at these points.

Image Reconstruction Algorithm

The image reconstruction algorithm that is used in the above described apparatus and system can be based on the iterative algorithm first described by *Paltauf et al.* in his paper entitled "Iterative Reconstruction Method for Three-Dimensional Optoacoustic Imaging" which is incorporated herein by reference.

The main assumption of the *Paltauf et al.* model is that the PA pressure profile measured at each detector can be described as a linear superposition of individual PA pressure profiles generated by spherical sources located on a three-dimensional grid of voxels. In the forward model, each spherical source generates a pressure profile given by:

$$p(\tau = t - r/c) \propto \frac{1}{r} \cdot \begin{cases} -\tau, & |\tau| \leq \frac{R_s}{c} \\ 0, & |\tau| > \frac{R_s}{c} \end{cases}, \quad (1)$$

where p is the magnitude of the pressure wave propagating radially from the center of the source, c is the speed of sound, r is the distance between the center of the source and the detection point, and $R_s$ is the radius of the spherical source. The pressure profile has a bipolar shape with a triangular positive compression phase followed by an inverted negative triangular tension phase.

The velocity potential (VP) is obtained by integrating the pressure profile with respect to T, and has the form:

$$VP(\tau) \propto \frac{1}{2r} \cdot \begin{cases} \frac{R_s^2}{c^2} - \tau^2, & |\tau| \leq \frac{R_s}{c} \\ 0, & |\tau| > \frac{R_s}{c} \end{cases}, \quad (2)$$

where the VP is a positive inverted parabola, peaking at T=0 and dropping to zero when T=±$R_s$/c.
For a given detector located at position $r_i$, the VP calculated for a PA source located at $r_j$ can be written as:

$$VP_{ij}(t) = \frac{W_j A_{ij} BF_{ij}(t)}{r_{ij}}, \quad (3)$$

where $W_j$ is the intensity of source j, $r_{ij}$ is the source-detector separation, $A_{ij}$ is the sensitivity matrix element indicating the relative sensitivity of detector i to a source at location $r_j$, and $$BF_{ij}(t) = \frac{3c^3}{4R_s^3} \begin{cases} \frac{R_s^2}{c^2} - \left(t - \frac{r_{ij}}{c}\right)^2, & \left|t - \frac{r_{ij}}{c}\right| \leq \frac{R_s}{c} \\ 0, & \left|t - \frac{r_{ij}}{c}\right| > \frac{R_s}{c} \end{cases} \quad (4)$$

is a unit area parabolic basis function of the same shape as (2), centered in time at $r_{ij}/c$.

When multiple sources are present, the total $VP_i(t)$ measured at detector i is obtained by summing equation (3) over all the sources (index j). Note that, in general, $BF_{ij}(t)$ is inserted into $VP_i(t)$ at different time points for each source.

The back-projection model is based on the assumption that each VP time point $VP_i(t_k)$ is a result of a linear superposition of sources that lie on a shell around detector i whose distance from the detector is in the range $c \cdot t_k - R_s < r_{ij} < c \cdot t_k + R_s$.

The amount of signal back-projected into each voxel j is given by $$\Delta W_j(t_k) = \frac{r_{ij}}{A_{ij} BF_{ij}(t_k)} \cdot \frac{VP_i(t_k)}{n_i(t_k)}, \quad (5)$$

where $n_i(t_k)$ is the number of voxels that are crossed by the shell defined by $t_k$. Note that in practice, $\Delta W_j(t_k)$ is set to zero when $BF_{ij}(t_k)$ drops below a threshold to maintain stability in $\Delta W_j(t_k)$ for voxels that lie on the edge of the shell.

Experimentally, the measured PA signals are rectified and filtered with a time-domain moving average to compute $VP_i^{exp}(t)$. A first estimate of the master image is formed by setting all voxel intensities to zero. The master image is forward-projected to obtain $VP_i^{est}(t)$. The difference $VP_i^{exp}(t) - VP_i^{est}(t)$ is calculated and back-projected into volume space. The resultant difference image is added to the master image and the outcome is forward-projected to obtain the new $VP_i^{est}(t)$. The iterative process was repeated until either one of two stop criteria is met: (i) a set number of iterations is reached, or (ii) a relative change in $VP_i^{exp}(t) - VP_i^{est}(t)$ between successive iterations drops below a given threshold.

In practice the sensitivity map of the detector array is interpolated and used as the weighting function $A_{ij}$ for the forward and back-projections. This map attenuated VP estimates from voxels where detector sensitivity is low and enhanced VP estimates from voxels where detector sensitivity was high.

Figure 38:
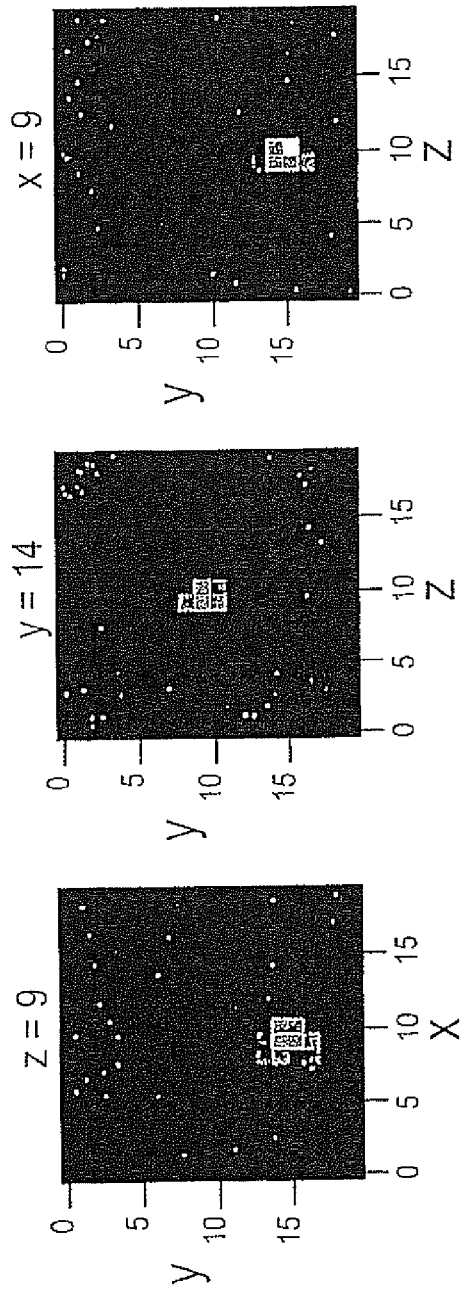
FIG. 38 illustrates three orthogonal sections of the reconstructed volume obtained from reconstructing the PA point source at one of the calibration scan points using the sparse array shown in FIG. 5.
Figure 39:
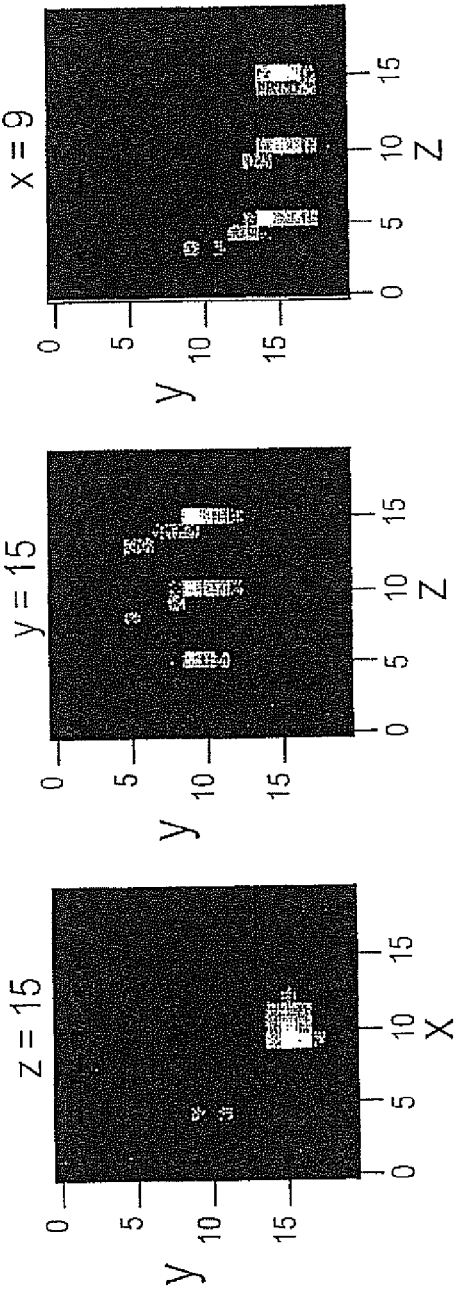
FIG. 39 illustrates orthogonal slices when synthetic sources are arranged along the indicated axis showing the three synthetic sources arranged along the z axis.
Figure 40:
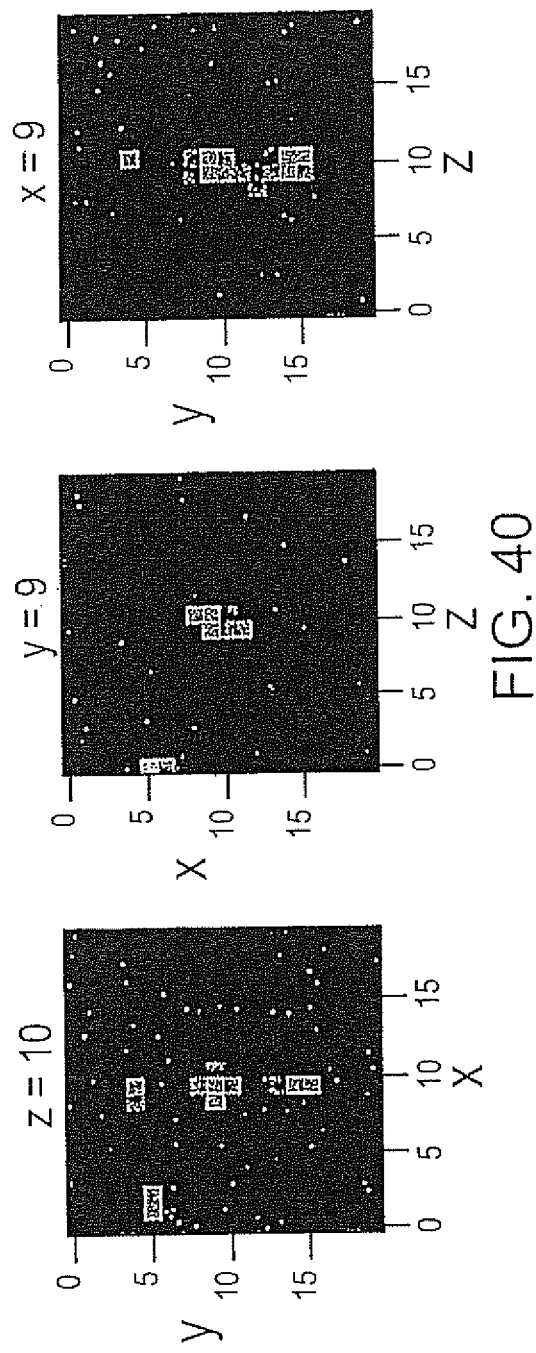
FIG. 40 shows three orthogonal slices similar to those in FIG. 39 where the sources were separated along the y axis.
Figure 41B:
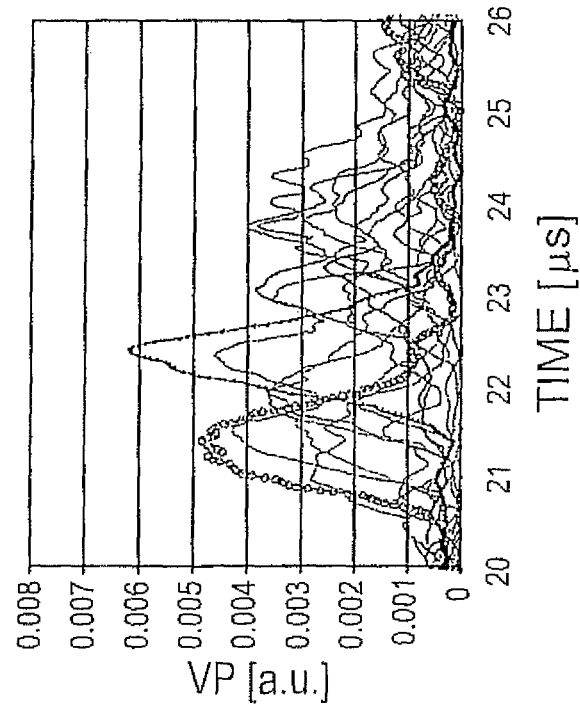
FIGS. 41a and 41b are graphs of the measured and reconstructed VP's versus Time respectively illustrating the results when a point source is imaged using backward mode illumination.
Figure 41A:
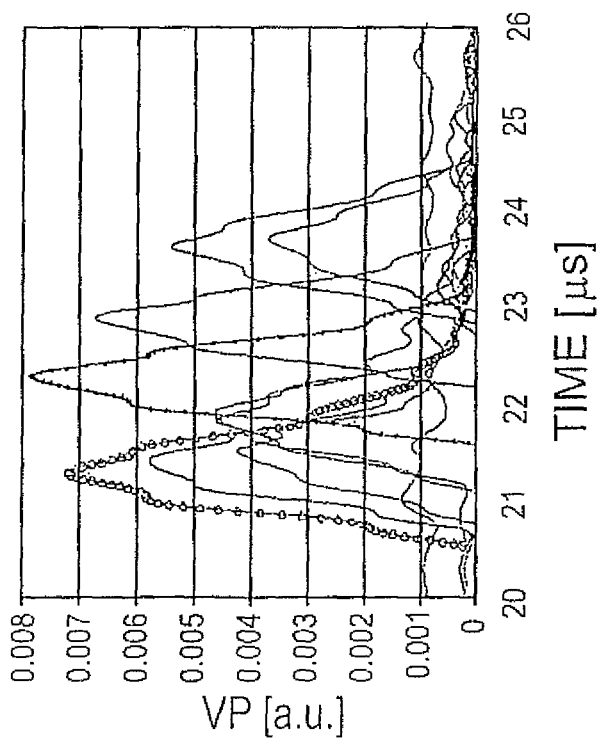

The images shown in FIGS. 38-40 were collected using the transducer array in FIG. 5 and reconstructed with the following algorithmic parameters: image volume of 20 mm×20 mm×20 mm, voxel size of 1 mm×1 mm×1 mm, Cartesian coordinate system as defined in FIG. 5 and 500 iterations. The choice of 500 iterations was to achieve a reasonable level of convergence of the image reconstruction algorithm in a reasonable length of computer processing time. Clearly, better results could be obtained by using a greater number of iterations (e.g. 2000 is described below). However, at some point continued iteration of the reconstruction algorithm will fail to give improved results. In practice, this depends on a variety of factors, including, but not limited to, complexity of the image, quality of the calibration scan results, precision of the computations, and selection of the basis functions. The relative voxel intensities are displayed on a linear grey scale.

Figure 20:
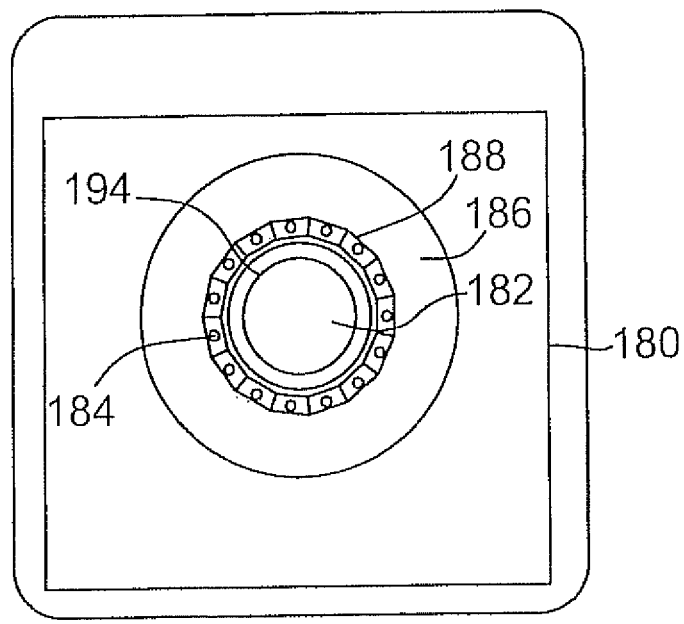
FIG. 20 is a top view of an annular transducer array for PA imaging.
Figure 21:
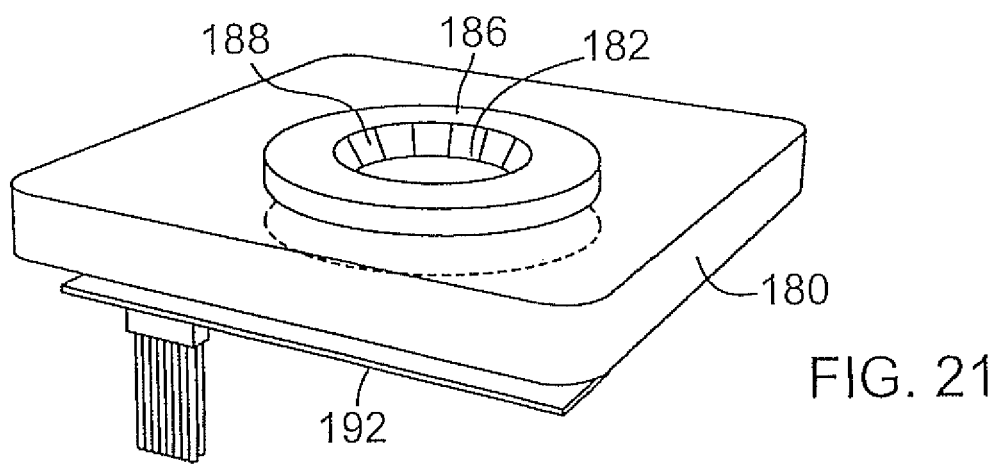
FIG. 21 is a perspective view, seen from above and two sides, of the transducer array of FIG. 20.
Figure 22:
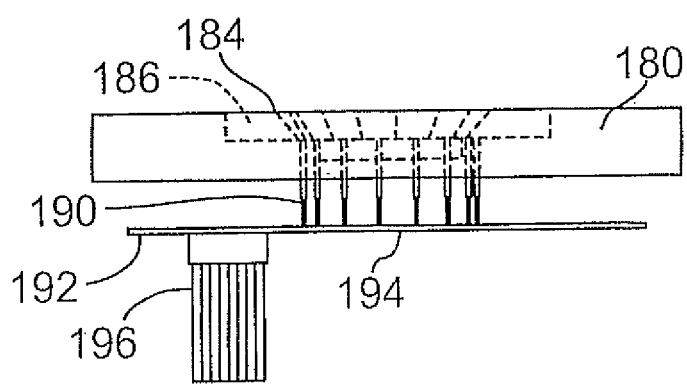
FIG. 22 is a front view of the transducer array of FIG. 20.

FIGS. 20 to 22 illustrate a particularly, exemplary version of an annular detector array and a horizontally extending support therefor. In this version, the annular array is mounted in a rectangular or square sample table 180 which itself is fixedly mounted to a suitable support (not shown). The sample to be imaged, which is not shown in these figures, is placed on top of the sample table. Located in the center of the table is a clear optical window 182 that transmits the laser illumination from below the table. The detection elements in the form of transducers 184 are embedded into the table top being distributed evenly about the window. Each transducer in this embodiment is 3 mm in diameter and they are arranged along a circle or ring having a 30 mm diameter. An acoustic lens 186 is integrated into the table top and has a wedged part 188 positioned directly on top of, and in acoustic contact with, the transducers 184. Each transducer is electrically connected via an individual pin-socket attachment 190 to an electronic card 192 underneath this unit which can be both a preamplifier and a filter card. This card has a cut-out at its center 194 to allow the laser light through the card. The card is able to amplify and filter the signals and then transmit them through a cable 196 to the aforementioned data acquisition system 18.

Figure 23:
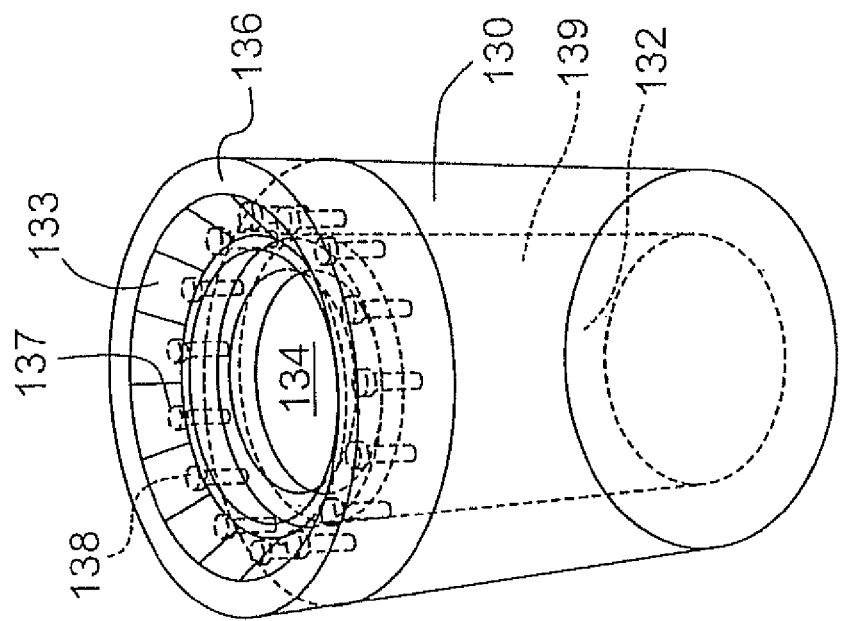
FIG. 23 is a perspective view of a handheld 3-D PA imaging wand.

The PA imaging apparatus and system as described above can be modified so as to provide a handheld imaging device for a physician/technologist for localized 3-D PA imaging of patients in a manner similar to that currently used on ultrasound patients. FIG. 23 shows a schematic view of a handheld 3-D PA imaging wand 130 with positional/angular transmitter located in a handle 132 to facilitate the imaging of a larger 3-D volume by handheld scanning of the wand. With knowledge of the wand orientation and position, the 3-D images collected from different perspectives can be stitched together. At one end of the wand is an access port 134 with a window for the laser beam of this unit. On the end of the wand is a focusing ring 136 in which are mounted a circular array of detector elements 138 which are spaced apart as shown. In this embodiment, the laser beam enters the wand via a fiber optic cable, passes through a longitudinal passage 139 down the length of the handle 132, and exits the window collinear with the axis of the ring. As shown, the detectors are arranged as an annulus and the directional sensitivity of each detector is steered towards the axis of the annulus by means of the focusing ring. Sound waves from the environment in response to the laser beam travel to the surface of the transducer array at each facet 133. The faceted surface redirects the sound waves towards the piezoelectric material which forms the transducer element 138. This material converts the wave to a voltage signal which is transferred to the electronics mounted within the handle 132 by means of a conductor 137.

Figure 24:
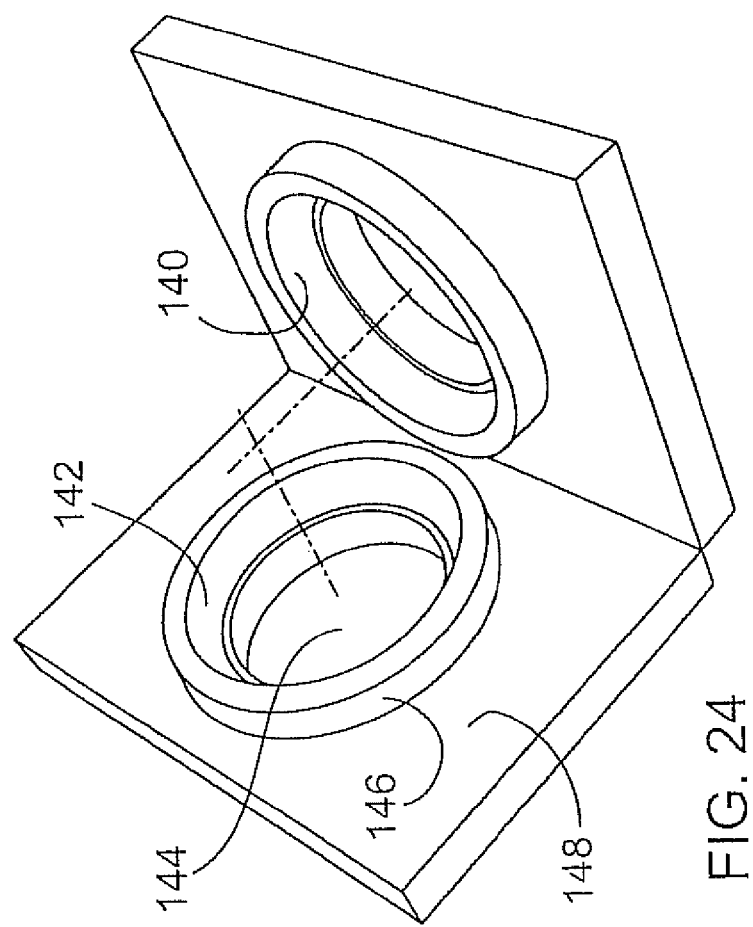
FIG. 24 is a perspective view illustrating two transducer arrays on different perpendicular planes, these arrays providing overlapping views of a 3-D imaging volume.

FIG. 24 illustrates an imaging apparatus which can be used in conjunction with the above described apparatus and system for PA imaging. In this version, there are two detector arrays mounted in the rings 140 and 142 which are in different planes to facilitate overlapping views of a 3-D imaging volume. As shown, the two array rings are in planes perpendicular to each other. Although the transducer elements of each array are not shown in FIG. 24, it will be understood that they are arranged in a manner similar to the detectors 138 shown in FIG. 23. Each array extends around an access port 144 fitted with a window for the laser beam. The detector elements are fixedly mounted on each ring which is mounted on a respective support plate 148. It is also possible to construct a PA imaging apparatus with more than two arrays located on the same or different planes.

Figure 25:
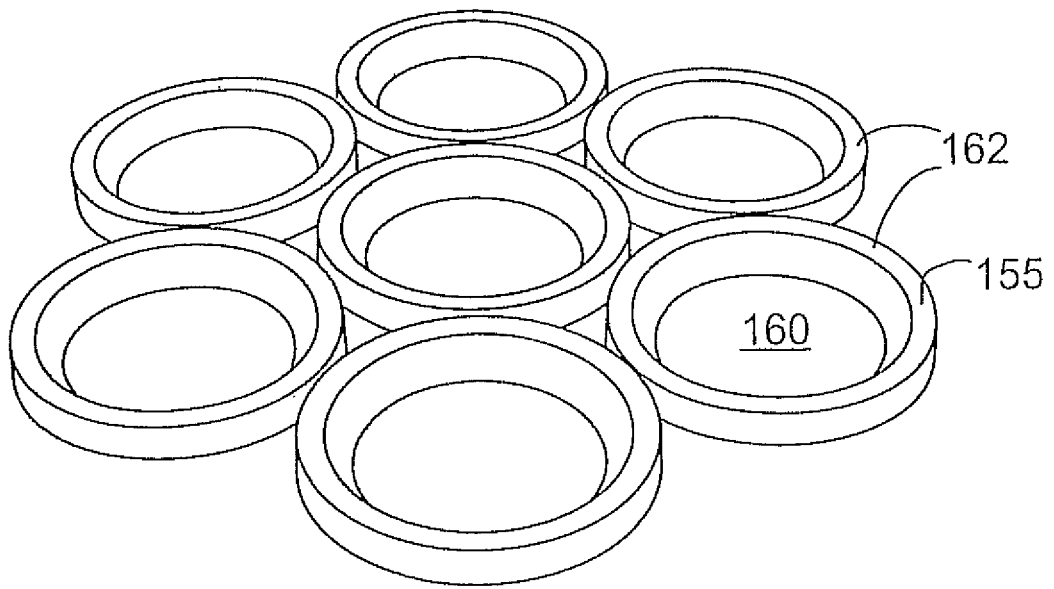
FIG. 25 is a schematic perspective view illustrating multiple annular transducer arrays arranged in the same plane to provide PA imaging of a larger 3-D imaging volume.

FIG. 25 illustrates a multi-ring version of an apparatus for illuminating a subject or specimen for purposes of PA imaging using the system described above. As shown, this version has seven detector arrays 162 arranged on a surface (plane as shown but bowl shaped is also possible) to facilitate the imaging of a larger 3-D imaging volume than a single ring can accommodate. As shown, there is a central array and extending about this central array are six annular arrays. A multi-ring version of this type can have fewer transducer arrays or more than seven detector arrays, depending on the application requirements. Each array is mounted on a focusing ring 155 which extends around an access port with a window 160 for a portion of the laser beam. Separate portions of the beam can be delivered to each array by splitting the laser beam using beam splitters or fiber optic cables in a manner well known in the laser beam equipment and fiber optic industries. The beam portions are delivered simultaneously to the windows 160.

Figure 26:
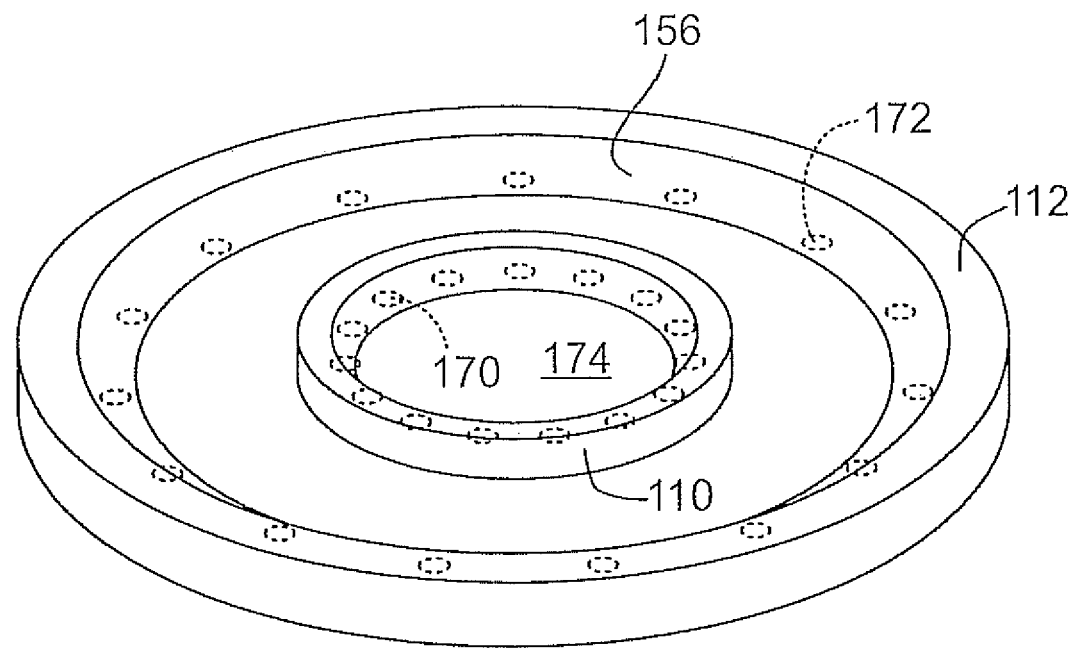
FIG. 26 is a perspective view of concentric annular transducer arrays capable of providing a second angular view of the imaging volume.

A further multi-ring version is shown in FIG. 26 which has concentric detector arrays 170, 172 in order to facilitate two angular views of the imaging volume. The inner array 170 is mounted on the inner focusing ring 110 while the outer array is mounted on the outer focusing ring 112. Located in and bounded by the inner ring 110 is an access port 174 with the window for the laser beam. Again, each ring has an inner wedge surface 156 for focusing purposes. The laser beam can be delivered to the arrays in the manner described above.

The use of several concentric detector rings is also possible, each with different combinations of geometric parameters. The use of such rings can achieve greater flexibility. In the version of FIG. 26, the detector rings 110, 112 can be designed to focus on the same spot, which provides higher sensitivity and resolution limited to a small volume. In a second version, construction of a set of concentric ring detector arrays with an inverse relation between the ring diameter and focal distance can achieve a "collimated" coverage field. From a manufacturing point of view, there is a strong advantage to the wedge method compared to a curved surface array. Machining of wedge surfaces is simple with modern CNC technology. Additionally, there is no need to modify the electronics or sensor material if a detector array of a different focal distance is desired; one only need change the wedge with another of a different wedge angle. This permits flexibility and a modular approach to detector design.

Figures 27, 28:
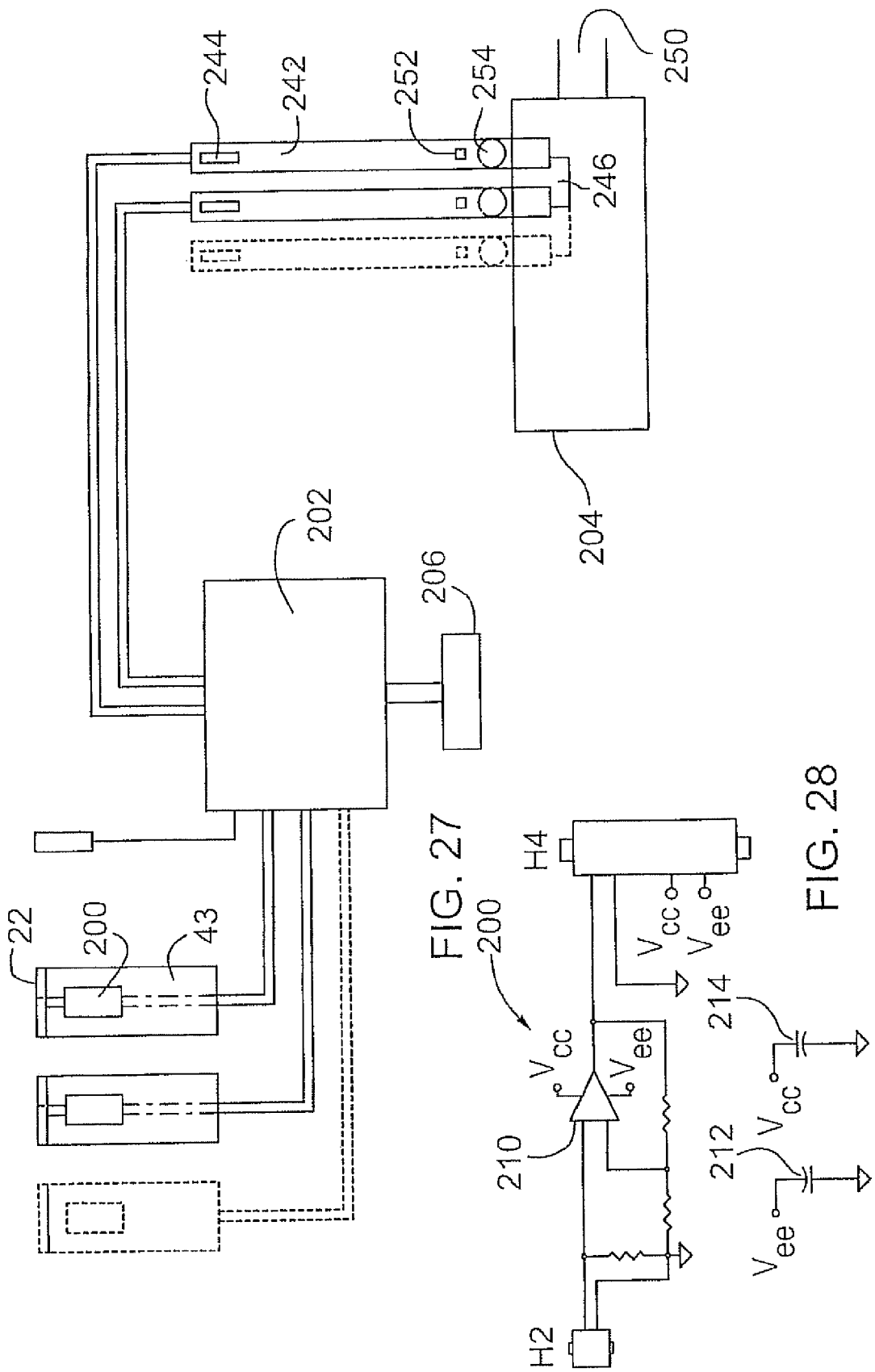
FIG. 27 is a schematic illustration of electronic components for the PA imaging system.
FIG. 28 is a circuit diagram of a preamplifier for each modular transducer.

FIG. 27 is a PA electronics block diagram that depicts three main electronic subsystems of the PA apparatus of the present disclosure beginning on the left with the piezoelectric transducers 22. The acoustic signal created by the illumination of the laser beam is converted to a weak electrical signal by each of the piezoelectric transducers and is immediately buffered by a preamplifier 200 located in the transducer body 43. This low noise preamplifier is configured as a high input and low output impedance device and receives power from a high-pass filter board or card 202. The signal is passed via a four conductor twisted ribbon cable to the sixteen channel high-pass filter of the card 202 which attenuates frequencies below 2 KHz and provides low noise gain. This filter can be configured when built for various cutoff frequencies and gain. The board also includes a pin diode amplifier (light detector) and can be jumper selected as channel 16. This signal provides timing and laser intensity information for the reconstruction algorithm. The filter board can stand alone or occupy one of the slots in a sixteen card chassis 204. Also shown is a power supply 206 which is electrically connected to the filter board and which in one embodiment is a ±5 volt supply.

With reference to FIG. 28 which illustrates the circuit for the preamplifier 200 that is provided with each transducer, it will be understood that the underside of the piezoelectric film which forms each transducer is directly connected to a non-inverting input of a high input impedance op-amp U1 210. The upper surface of the transducer is connected to ground and to a copper shield surrounding the preamp 200. The preamp is configured as a low gain non-inverting amplifier and serves mainly to match the high impedance of the detector to the lower impedance of the filter input. This also overcomes high frequency signal loss due to stray capacitance of the signal wire. The op-amp power leads are bypassed by C1 and C2 shown at 212 and 214 to ensure no signal loss or spurious oscillations. Power and signal is conducted over a two pair twisted cable to the filter board 202.

Returning to FIG. 27, the filter board 202 in an exemplary embodiment is made with sixteen identical channels of high-pass filters with gain (80 dB) plus one pin diode amplifier which serves as a light detector. It also includes low voltage regulators and power indicator LED's. The following description applies to channel 1 shown in the upper left corner of FIG. 29(a) and its light detector but it will be appreciated that each channel is similar in its construction.

Each filter uses a dual op-amp configured as a 3 pole Butterworth high-pass filter having a gain set between ×2 and ×16. Input to the first stage is through C1 indicated at 220 in FIG. 29(a) and gain is selected in this stage by choice of R2 located at 222. A feedback resistor R3 is chosen by recommendation of the op-amp vendor. Capacitors C2 at 226 and C3 form poles 2 and 3 feeding a unity gain output stage. All power pins are well bypassed by capacitors (not shown). The filters provide −85.3 dB at the stop band and −3 dB at the passband which extends beyond 20 MHz.

Figure 29:
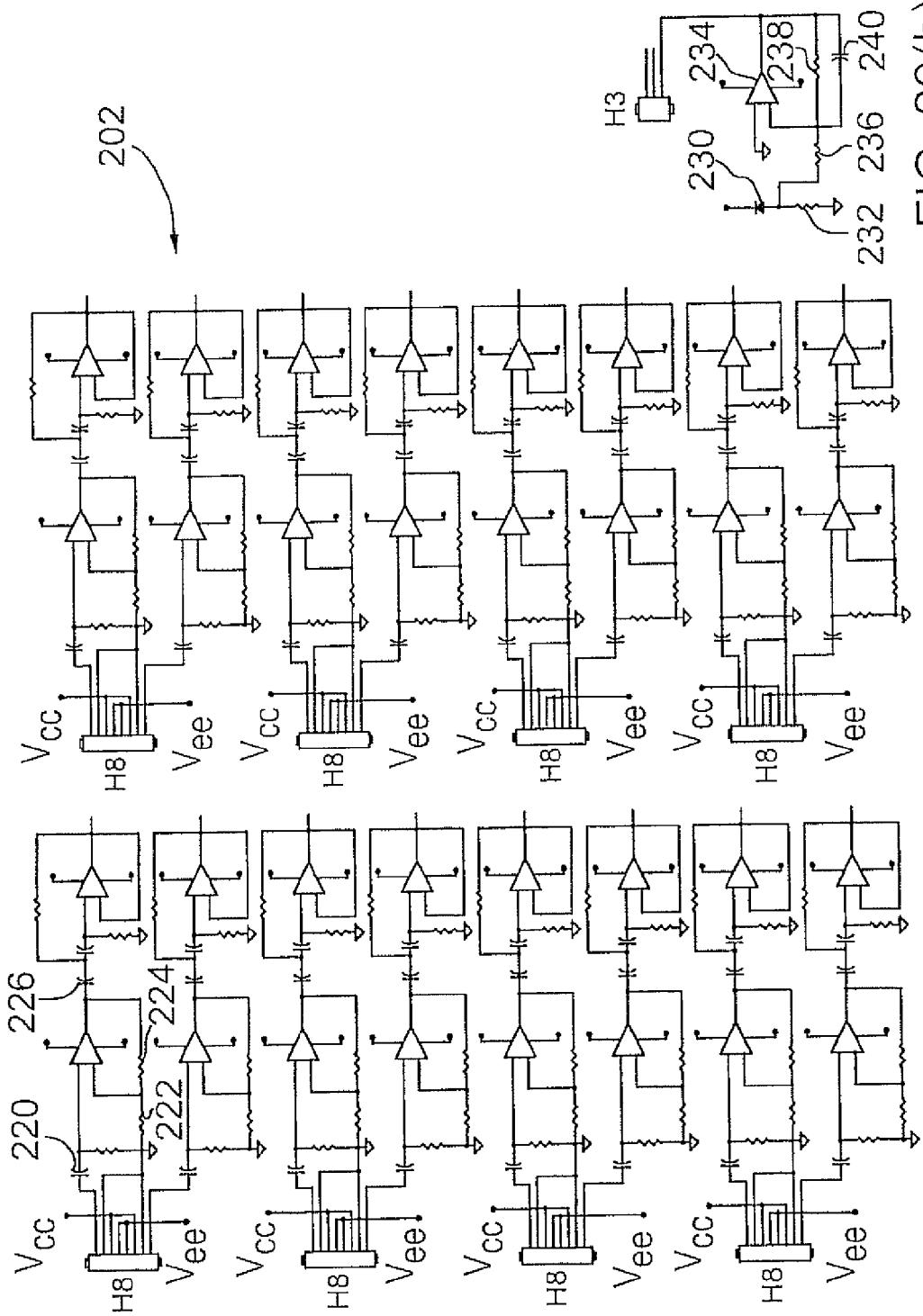
FIGS. 29a and 29b are circuit diagrams for a filter card for the PA imaging system, this card including amplification.

The light detector is formed with pin diode D1 indicated at 230 in FIG. 29(a) and a bias resistor R73 indicated at 232 connected to an inverting amplifier U17B shown at 234 with a gain of ×10 determined by R74 located at 236 and R75 located at 238. Signal integration may be achieved with capacitor C49 located at 240 but testing has indicated that it may not be required.

After signal conditioning is done by the filter card, the signals pass via sixteen conductor twisted ribbon cables to digital converter (ADC) cards 242. These cards are arranged as 8 channels per card and contain four pole anti-alias filters connected to 14 bit, 65 Msps ADC's. Arranged on each of these cards is a low pass filter 244. The converters are clocked at 50 MHz and the output is latched into 512 K sample buffer sequential access memory. One card provides a master clock (indicated at 246) and trigger signal while subsequent boards are slaved. The trigger signal from the laser is passed to all cards and provides the converters with a common start signal.

This ensures all channels acquire data at precisely the same time. An onboard MPU initializes the converters to a selected mode, enables the trigger, tracks the number of samples acquired and transmits the data to either the USB port or high speed parallel port, but is not directly involved in the acquisition of data. The 8 channel ADC cards can be fitted into a twenty-one slot VME bus rack that provides power, passes clock signals and provides a high speed parallel bus for data/control, this bus being indicated at 250. The power supply provided by the chassis 204 can be a ±15 volt power supply. This system enables up to 128 channels of data acquisition to occur simultaneously. Also shown in FIG. 27 are USB data/control ports 252 and laser trigger inputs 254 provided on the ADC cards.

There are also commercial electronic products that can be used instead of the described circuit boards. Instead of the pre-amplifier illustrated in FIG. 28, there is available Olympus NDT Model 5660 B (single channel only). Details are available at Internet website www.olympusndt.com/en/preamplifiers/. An alternative digitizer is National Instruments Model PXIe-5122 (100 MS/s, 14-bit, 2 channels only).

Figure 30:
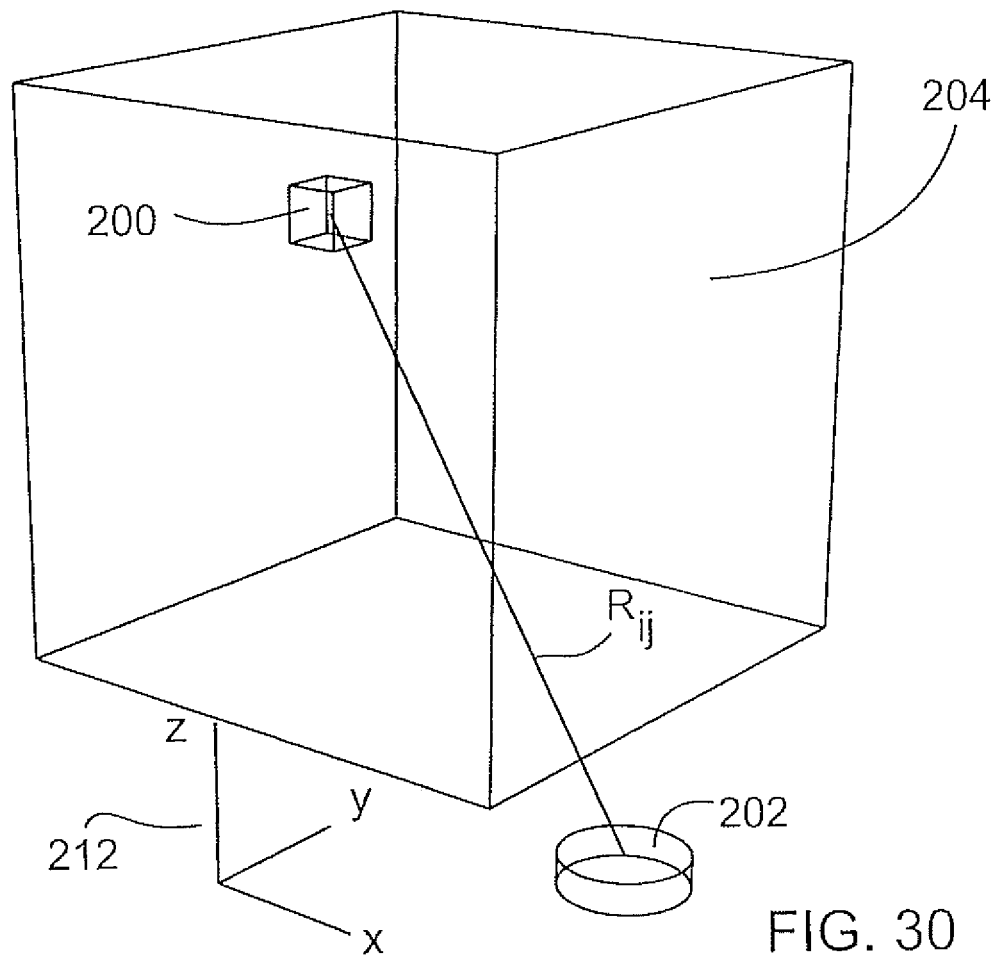
FIG. 30 is a schematic diagram that describes the geometrical relationship between a voxel position and a transducer position.
Figure 31:
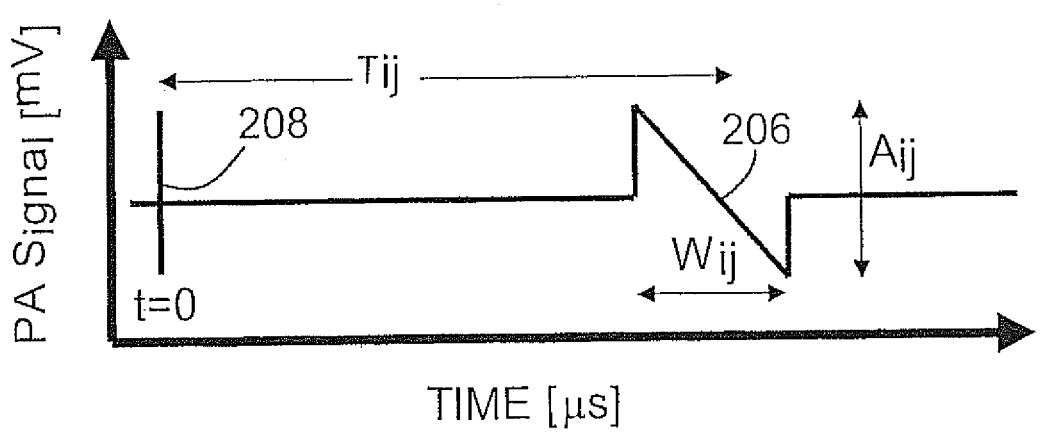
FIG. 31 is a schematic representation of the PA signal indicating the parameters of arrival time, temporal width and amplitude that are derived from the calibration scan.

The geometrical relationship between a voxel 200 and a transducer element 202 relative to a coordinate system 212 is described in FIG. 30. For a given imaging volume 204, there will be a multitude of voxels 200. For a given ultrasound transducer array, there will be a multitude of transducer elements 202. Considering the $i^{th}$ voxel with center at position $(x_i, y_i, z_i)$ and the $j^{th}$ transducer element with acoustic center point at position $(x_j, y_j, z_j)$, the PA signal from the calibration scan using an apparatus in FIG. 9 will have the appearance of an "N"-shaped signal at an elapsed time $T_{ij}$ after the laser pulse. The PA signal is shown in FIG. 31. Time series analysis on the signal is used to determine the peak-to-peak amplitude of the PA signal represented by $A_{ij}$, the temporal width $W_{ij}$, and the temporal location of the PA signal $T_{ij}$ relative to the laser pulse. For the $j^{th}$ transducer element, the distance $R_{ij}$ to the $i^{th}$ voxel is given mathematically by the expression:

$$R_{ij}=[(x_i-x_j)^2+(y_i-y_j)^2+(z_i-z_j)^2]^{0.5}$$

Using the result from the calibration scan, a measured estimate of $R_{ij}$ is determined by:

$$R'_{ij}=cT_{ij}$$

where c represents the speed of sound in the medium between the $i^{th}$ voxel and the $j^{th}$ transducer element.

Figure 32:
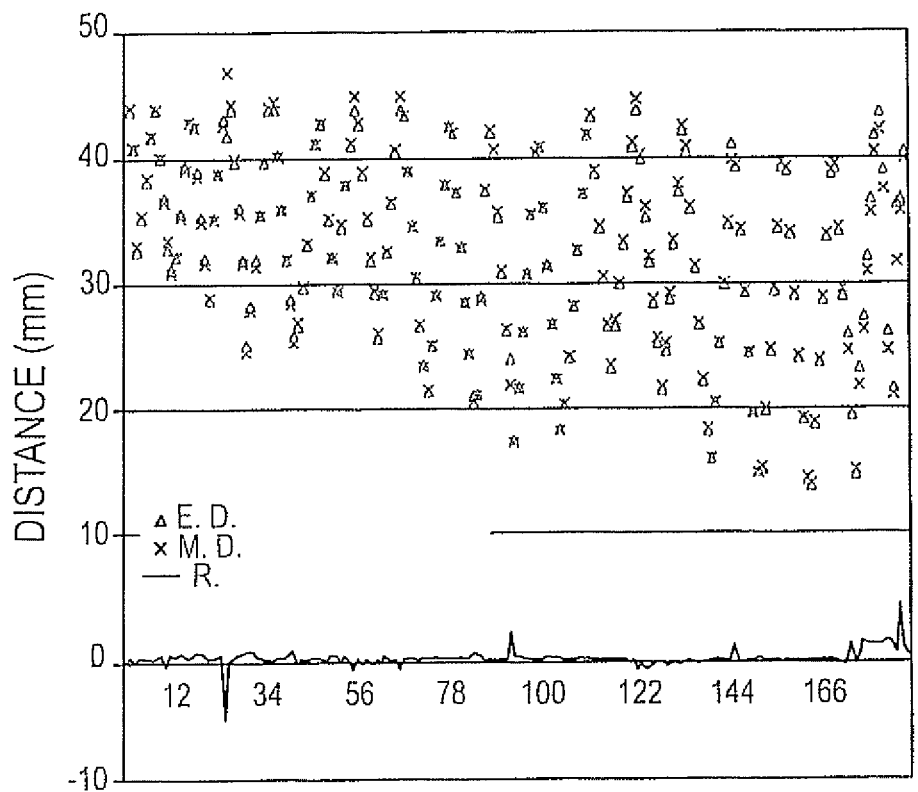
FIG. 32 is a graph of the distance (D) in mm to one specific detector (No. 7) measured for all the voxels in the volume during the calibration scan using the apparatus of FIG. 9 and estimated by a non-linear parameter estimation technique related to FIGS. 30 and 31.

For these relationships, the position of the $i^{th}$ voxel is known due to prior knowledge of the position of probe tip 84 that acts as the PA source connected to the 3D gantry 88 shown in FIG. 9 during the calibration scan. Therefore, estimates of $R_{ij}$ can be made by estimating the position of the $j^{th}$ transducer element. Comparison of $R_{ij}$ to $R'_{ij}$ (i.e. the estimate based on the measurement from the calibration scan) provides an estimate of the residual (i.e. error). A multitude of residual estimates are obtained by calibration scan measurements at a multitude of voxel locations. The technique of nonlinear parameter estimation (e.g. nonlinear least squares curve fitting) is used to minimize the residuals to provide an accurate estimate of the $j^{th}$ transducer element position. This method is repeated of each transducer element in the transducer array and provides an estimate of the position of each transducer element relative to the imaging volume. FIG. 32 shows the estimated detector to transducer element distance $(R_{ij})$, the measured estimates of the detector to transducer element distance (c $T_{ij}$) and the residuals for a typical sensitivity scan of 187 voxel positions for a transducer array similar to that shown in FIG. 5. In this case, nonlinear least squares fitting was used to estimate the position of the $7^{th}$ transducer element. Data for the remaining 13 transducer elements was similarly obtained but not shown for clarity.

An alternative reconstruction algorithm to the modified version of Paltauf described above is presented below. The objective of the reconstruction algorithm is to estimate a distribution of voxel intensities $w_i$ in the imaging volume 204 by iterative fitting of a model PA signal to the measured PA signal (or measured VP) $M_{jk}$ from each transducer element. This is accomplished by mapping (forward projecting) a scaled value of a basis function $BF_{ijk}$ representative of the PA signal (or VP) into the time domain for the $j^{th}$ transducer element. Scaling is done by multiplying $BF_{ijk}$ by the estimated voxel intensity $w_i$. The index k represents the time index of the discretized basis function where k is in the range of 0 at laser pulse to K at the end of the data acquisition period. Example shapes of the basis function are Gaussian, parabola, triangular, rectangular, N-shaped, cosine, sinusoid, based on parameter data obtained from the point source during the calibration scan, based on time scans of the point source at the $i^{th}$ voxel, etc. The basis functions will generally be dependant on $T_{ij}$, $A_{ij}$, and $W_{ij}$ determined during the calibration scan at the $i^{th}$ voxel. However, other parameters from the calibration scan could be incorporated. For each transducer element, an estimated signal representative of the summation of basis functions representative of all voxels in the imaging volume is computed $S_{jk}$. With basis functions designed to represent the pressure signals, the summed signed $S_{jk}$ will be further processed by an integration step or alternatively rectification followed by low pass filtering. Next, a differential signal $D_{jk}$ is computed by subtracting the summation signal $S_{jk}$ from $M_{jk}$ at the $j^{th}$ transducer element and the $k^{th}$ time sample. The $k^{th}$ sample of $D_{jk}$ for the $j^{th}$ transducer element is multiplied by a factor $p_{ijk}$ and the product added to the $i^{th}$ estimated voxel intensity $w_i$. Negative values of $w_i$ are then set to zero (0). This process is repeated for all values of i, all values of j, and all values of k. The resultant estimated image is then used as the input for the next estimation of the PA signals (or estimated VP signals) $S_{jk}$ by the basis function approach. The process continues iteratively in a manner analogous to the algorithm described in FIG. 7 until a stopping criteria (i.e. negligible change in the error or predetermined number of iterations) is reached. The factor $P_{ijk}$ is computed before the reconstruction starts using the results of the calibration scan and basis function selection and represents a normalization factor. The resultant image is converted to a format suitable for graphical display by image viewing software.

An alternative and more general reconstruction algorithm to the modified version of Paltauf et al described above is presented in FIG. 34. The objective of the alternative reconstruction algorithm is to estimate a distribution of voxel intensities $w_i$ in the imaging volume 204 shown in FIG. 30 by iterative fitting of model PA signals $S_{jk}$ to the measured PA signals (or derived VPs) $M_{jk}$, where i is the voxel index, j is the transducer index, k is the time index, and $S_{jk}$ and $M_{jk}$ represent the elements in separate two-dimensional matrices. The voxel index i ranges from 1 to V, where V is the number of voxels in the image. The transducer index/ranges from 1 to M, where M is the number of transducers in the array. The time index k ranges from 1 at laser pulse to N at the end of the data acquisition period.

Before the first iteration, all measured values of $M_{jk}$ are inputted (indicated by 296) with or without preprocessing (i.e. if conversion to VP is desired as described below) and all values of $w_i$ are initalized to zero (0), some other suitable constant value, or image data from a previous reconstruction. The algorithm proceeds in step 298 by forward projecting all values of $w_i$ into the time domain to generate a two-dimensional matrix of estimated signal values with elements represented by $S_{jk}$. If basis functions representative of the pressure signals are used during step 298, then the signal estimates are converted to VP estimates by further processing and replacement of all values of $S_{jk}$ by the result of numerical integration, rectification, or rectification followed by low-pass filtering on the matrix of signal estimates. Next, in step 300, a two-dimensional matrix of residual values are computed using the relation $$D_{jk} = M_{jk} - \beta S_{jk} \tag{7}$$

where j is varied from 1 to M and k is varied from 1 to N and β is a scaling factor suitably chosen. At this point in the algorithm, a test of convergence is performed as indicated by step 302. One convergence metric (err) that works well in practice, is described by the relation, $$err = 100 \frac{\sqrt{\sum_{j=1}^{M} \sum_{k=1}^{N} (D_{jk})^2}}{\sqrt{\sum_{j=1}^{M} \sum_{k=1}^{N} (M_{jk})^2}} \tag{8}$$

The test for convergence involves comparing err from the current iteration to the value of err from the previous iteration. If the difference in err is below a preset value the algorithm returns the image estimates (indicated by 308) stored in the matrix with elements $w_i$ to the calling program so that the image data can be converted to a format suitable for graphical display and further analysis. (Several other approaches for controlling when the algorithm returns are possible, e.g. fixed number of iterations, tracking of individual errors for each transducer, etc.) If the difference in err does not meet the criteria, then the algorithm continues by back projecting the residual values in step 304 to obtain estimates of the differential voxel intensities represented by $d_i$. The residual voxel intensities are then used to update (step 306) the current estimates of the voxel intensities by the relations in sequence, $$w_i = w_i + d_i \tag{9}$$

$$w_i = \begin{cases} w_i, & \text{if } w_i > 0 \\ 0, & \text{if } w_i \leq 0 \end{cases} \tag{10}$$

where i is varied from 1 to V. The algorithm then proceeds to the next iteration as indicated in FIG. 34.

Figure 34:
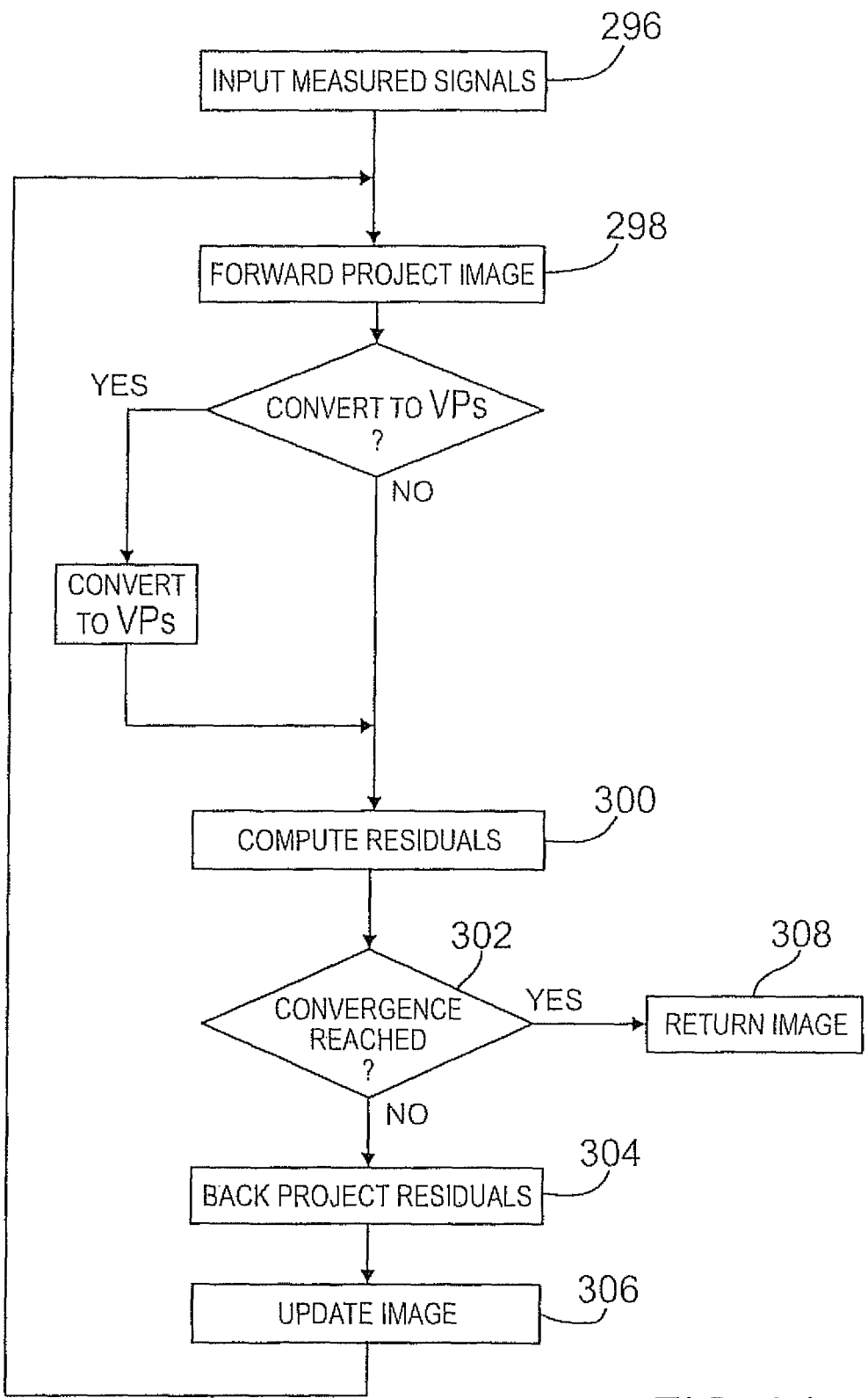
FIG. 34 is a flow chart of a reconstruction loop which is part of a reconstruction algorithm.

The algorithm for forward projecting the image indicated by 298 in FIG. 34 is now described. The forward projecting algorithm begins by receiving the current estimates of the voxel intensities represented by $w_i$. All values of $S_{jk}$ are set to zero (0). Next, an estimated signal $S_{jk}$ is computed using the relation $$S_{jk} = \sum_{1}^{\sigma} w_i BF_{ijk} \tag{11}$$

Figure 35:
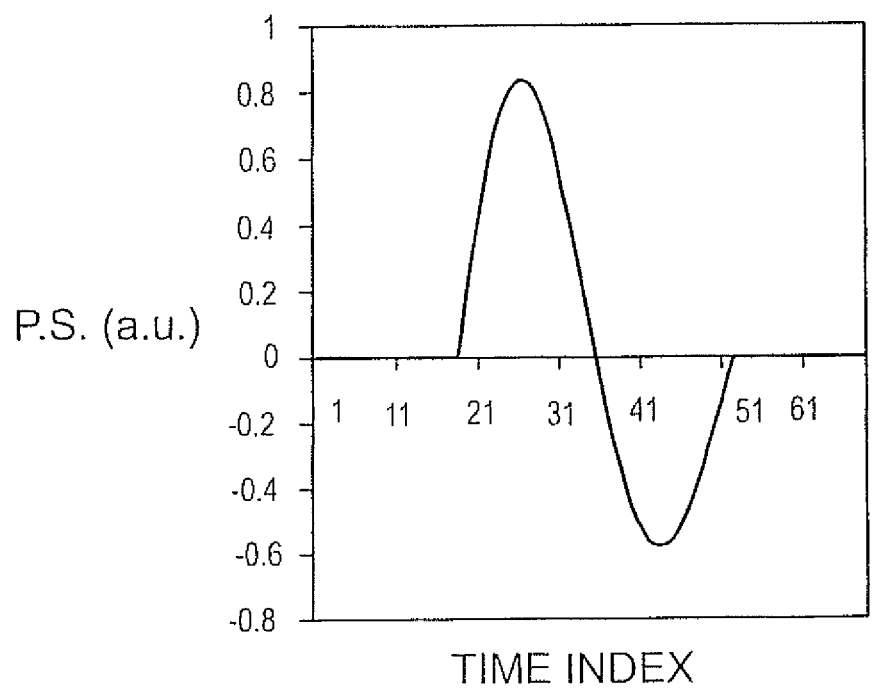
FIG. 35 is a times series basis function representative of a PA pressure signal modeled using a truncated damped sinusoidal function.

Signal values are computed for all values of j from 1 to M and all values of k from 1 to N. In Equation 11, the expression $BF_{ijk}$ represents the element of a three-dimensional matrix of basis functions. The signal values are then returned to the image reconstruction algorithm. The basis function array with elements $BF_{ijk}$ can be derived from mathematical functions, mathematical functions that utilizes measured parameter data, or time series data that are derived from experiment. Example mathematical functions include Gaussian, parabola, triangular, rectangular, N-shaped (as described by equation 1 above), cosine, sinusoid, and damped sinusoid. Examples of parameter data include, but are not limited to, $T_{ij}$ (i.e. measured time of flight of the PA signal), $A_{ij}$ (i.e. measured amplitude of the PA signal) and $W_{ij}$ (i.e. the measured temporal width of the PA signal) determined during the calibration scan at the $i^{th}$ voxel at the $j^{th}$ transducer using some or all T time points. Examples of parameter data are shown in FIGS. 14-16. However, in these examples, the calibration scans were performed for grid points that were separated by step size greater than voxel size in the image. To overcome this, the parameter data was interpolated; however a calibration scan employing a denser grid of points would be preferable. An exemplary mathematical damped sinusoidal basis function is given in FIG. 35. This example works well for modeling the PA pressure signals obtained with the PA imaging apparatus in combination with a time-shifting operation utilizing the above-mentioned $T_{ij}$ parameter data from a calibration scan. An example of the time series approach is to use directly as the basis functions the measured PA signals obtained at the $i^{th}$ voxel at the $j^{th}$ transducer during the calibration scan.

Details of the algorithm for back projecting the residual signals in step 304 of the image reconstruction algorithm described by FIG. 34 are now given. The process of back projecting each value of $D_{jk}$ to obtain the estimate of the differential voxel intensity is performed using the relation $$d_i = \sum_{j=1}^{M} \sum_{k=1}^{N} p_{ijk} D_{jk} \tag{12}$$

Figure 36:
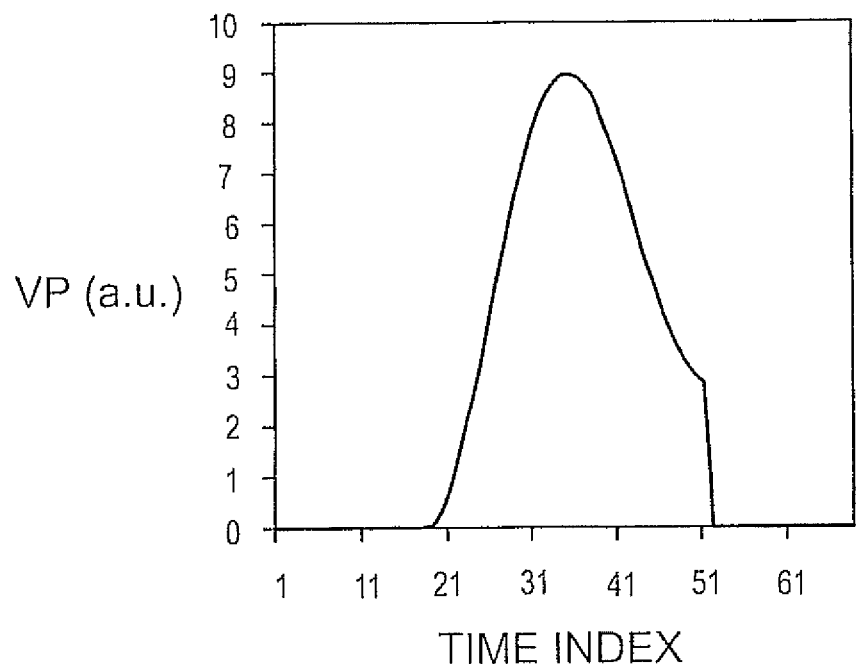
FIG. 36 is a times series backward basis function representative of a PA VP signal corresponding to FIG. 35.
Figures 37A, 37B:
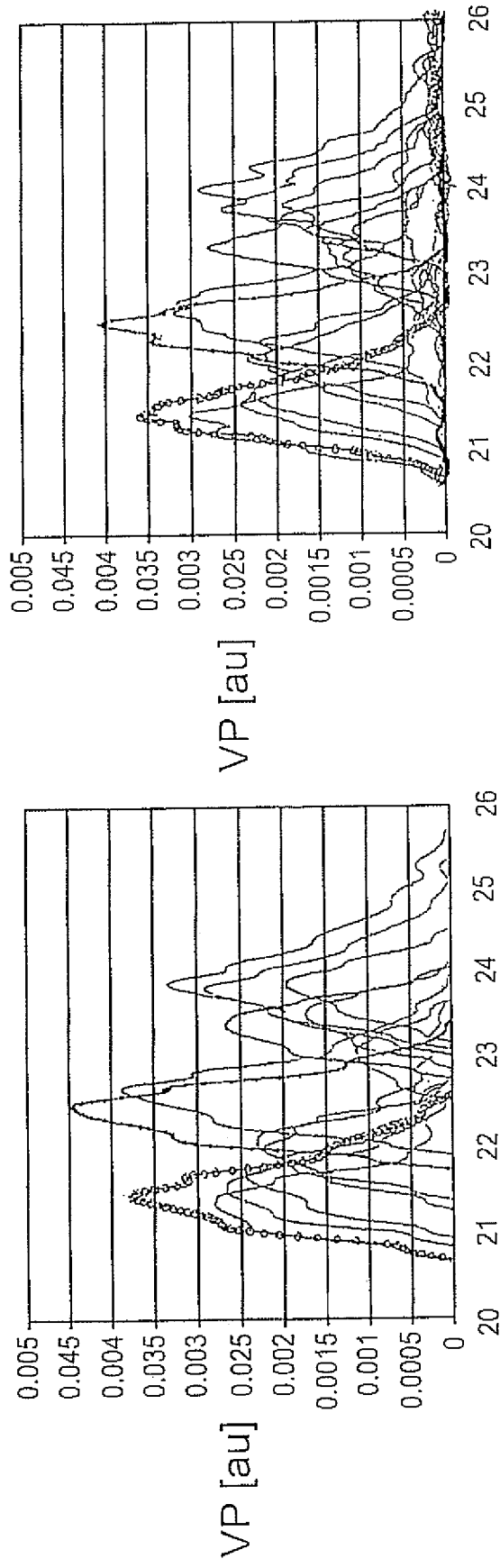
FIGS. 37a and 37b are graphs of velocity potentials (VP) versus Time with FIG. 37a displaying the VP's calculated from the measured PA signals and FIG. 37b showing the estimated VP's obtained from the image reconstruction algorithm after 2000 iterations.

Although several possibilities exist for construction of the three-dimensional matrix with elements represented by $p_{ijk}$, in practice the relation $$p_{ijk} = \begin{cases} \frac{1}{BBF_{ijk}}, & \text{if } |BBF_{ijk}| \geq \delta \\ 0, & \text{otherwise} \end{cases} \tag{13}$$

works well, where δ is suitably chosen to avoid division by zero (0). Here $BBF_{ijk}$ represents the element from a three-dimensional matrix of backward basis functions computed before the image reconstruction starts. Elements of the backward basis functions can be computed by integrating the basis functions in the time domain when mathematical functions are used or numerical integration (or alternative methods described above) in the event experimentally derived basis functions are used. Integration is only necessary if the basis functions used in the forward projection are representative of pressure signals (i.e. not VPs). An exemplary integrated basis function is shown in FIG. 36, where the function represents the integrated damped sinusoidal function from FIG. 35. Once all values of $d_i$ have been computed, the resultant differential voxel intensity estimates are returned to step 306 of the image reconstruction algorithm in FIG. 34. One point of note is that in general the three-dimensional matrices described by $BF_{ijk}$ and $p_{ijk}$ will be sparse and therefore techniques for accelerating the computations can be exploited. One skilled in the art will recognize that this image reconstruction algorithm will account for materials that may be placed between the subject and the transducer array and affect the coupling of PA waves from the subject to the transducer array. Examples of such materials are the plastic window structure indicated as 131 in FIG. 3 and the bowl indicated as 95 in FIG. 10. This property of the image reconstruction algorithm permits thicker and hence stronger holders and bowls to be used compared to the thin films described earlier.

3-D Imaging Results

FIGS. 37 through 42 demonstrate 3-D PA imaging with the sparse array approach using the annular array apparatus described in FIG. 5. FIG. 38 shows results of using the apparatus to reconstruct an image of a single synthetic point source. FIG. 37(a) displays the VPs calculated from the measured PA signals (see FIG. 12). The VPs were entered into the reconstruction algorithm as the target functions for the iterative reconstruction procedure. In FIG. 37(b), the estimated VPs obtained after 2,000 iterations (13 minutes run-time on the PC) are shown. Qualitatively, the magnitude and timing of the peaks were reproduced well (e.g. compare the highlighted channels in FIGS. 37(a) and 37 (b)). However, the peak shapes in the estimated VPs had some side lobes and a background noise level that were not present in the measured VPs. FIG. 38 presents three orthogonal sections of the reconstructed volume. The point source was reconstructed at the expected location. Some misregistered voxels were present, most notably in the yz plane, which correlated with the broadening of the estimated VPs. It is noted that the broadening was stronger in the x- and y-directions, while the edges were better defined in the z-direction.

An array of three synthetic sources arranged along the z-axis and three synthetic sources along the y-axis was reconstructed. As can be appreciated from the orthogonal slices, the sources along the z-axis (FIG. 39) were better defined and better separated than the ones along the y-axis (FIG. 40). This was to be expected from the way the annular-array detectors were arranged relative to the volume: A separation of 5 mm in the z-axis created a time-of-flight difference approximately two-times longer than the same separation along the y-axis. Therefore, the reconstruction algorithm was presented with well-separated peaks and hence was able to reconstruct sharper edges on the sources distributed along the z-axis. The images of the sources separated in y are presented in FIG. 40 and exhibited artifacts near the volume boundaries, which were not present in FIG. 39. The bright voxels at (x,y,z)=(5, 9,0) and (1,5,10) were the result of poor convergence by the iterative reconstruction algorithm, which could be a result of the algorithm being unable to find a voxel distribution that simultaneously reconstructs the time-domain measurements from all detectors. In these cases, the algorithm appeared to back-project signal into voxels that were further away from the detector, but was restricted by the volume boundary. Hence, part of the signal was deposited near the boundary resulting in these artifacts.

Finally, a point source with backward mode illumination was then imaged. The results are displayed in FIGS. 41 and 42. In this experiment, only 10 of the 14 detector elements recorded signals above the noise level. Although the exact cause of the signal dropout could not be determined, it may have been related to asymmetry in the PA wave generated by the source. Nevertheless, the algorithm was able to reconstruct the point source at the proper position even with signals from an incomplete set of detectors. By comparing the estimated VPs in FIG. 41(b) with the measured VPs in FIG. 41(a), it is clear that some detector signals that were not present in the measured VPs were present in the estimated VPs from the reconstruction algorithm. Comparison of the estimated VPs in FIG. 41(b) with the estimated VPs of the synthetic source detected by all 14 detectors (FIG. 37(b)) verified that the signals generated by the reconstruction algorithm had the correct timing as expected from the source-detector geometry. This indicates the robustness of the algorithm to missing or incomplete data (i.e. as long as most detectors can detect the PA signal, the algorithm is able to compensate for those that do not record signal). This may be helpful when objects with significant impedance as compared to soft tissue (e.g. air or bone) interfere with the sound propagation to the detectors.

The images obtained from a point source and an array of point sources confirmed localization accuracy of about 1 mm or less in each dimension. This validates the accuracy with which the positions of the array elements were registered to the imaging volume using the scanned PA source method. Analysis of line profiles through the point-source image (FIG. 42) along the lateral (x and y) and the depth axes (z) resulted in estimates of the point spread function (PSF) for the three coordinate directions of the imaging system. Image resolution was determined from the FWHM of the PSF. From this data the spatial resolution for the 3-D PAI system was ~1.5 mm in z and ~2.5 mm in both x and y. This estimated resolution at a depth of 30 mm compares well to other previously described systems using staring 3-D-PA imaging methods.

The images shown in the figures were reconstructed from data acquired over 10 laser pulses for averaging and noise reduction. Hence, image acquisition took 1 second (laser repetition rate was 10 Hz). Image reconstruction, however, took on the order of minutes (13 minutes for 2,000 iterations). Reconstruction computations scale linearly with number of transducers, and with number of voxels in the image. Faster reconstruction times are possible by reducing the resolution and/or specifying a smaller image volume.

4-D Imaging Results

For validating four-dimensional imaging capabilities, we imaged phantoms comprised of moving targets—a scanning point source and a rotating graphite rod. The scanning speed of the point source for both directions was measured during the experiment and was determined to be 4.5±0.2 mm/sec. The rotation experiment in water was carried out with a 0.9 mm diameter graphite rod, commonly used in mechanical pencils. The rod was held horizontally (parallel to the bottom of the tank) and was illuminated from below. The angular velocity of the rod was determined to be 120±4°/s. FIG. 44 shows results from the scanning point source experiment. PA movies of the target scanned in the positive y direction are presented both in 2-D (FIG. 44(a)) and in 3-D (FIG. 44(b)). The reconstructed shape of the point source was used to compute the Point Spread Function (PSF) of the imager. (The actual size of the source was ~0.4 mm$^3$). We estimated the PSF to be 2.0-2.5 mm in each direction. However, when the source location was close to the edge of the volume, the reconstructed shape became flattened, as can be seen in the left pane of FIG. 44(a). This effect of the finite reconstruction volume is due to boundary artifacts. It is also worth noting the change in the shape and relative intensity of the source even when it was well within the reconstruction volume. Although this change was not as drastic as that observed near the edge of the volume, it indicated variability in the imaging quality at different locations in the reconstructed volume.

FIG. 43 shows results from the rotating rod experiment. PA movies of the 0.9 mm rod rotated counter clockwise are presented both in 2-D (FIG. 43(a)) and in 3-D (FIG. 43(b)). The 2-D frames in FIG. 43(a) represented well the linear shape of the rod, with significant contrast to background. It was apparent from the sequence that the center of rotation shifted slightly between frames, which correlated to an actual wobble of the rod holder. The perceived diameter of the rod was ~3 mm. This corresponded to an increase of 2 mm relative to the actual diameter; in agreement with the estimated PSF. Frame #10 in FIG. 43(a) showed an example of an image artifact that appeared throughout the sequence. It presented as a ghost image of part of the rod, overlaid on the true image. The ghost image was probably a consequence of the piecewise reconstruction of boundaries by the sparse array. The intensity and quality of the reconstructed target varied significantly between frames. This was a combined result of the directionality of the acoustic waves emitted from the rod and the piece-wise detection of the sparse array. In order to test the quality of image representation, the 2-D movie of the rotating rod was analyzed to determine the perceived rod movement through the sequence of images. This was achieved by visually fitting a line to the image of the rod in each frame and recording its angle relative to the x-axis. As the rod rotated counter clockwise, the angle increased between frames. We expected the angle to increase at a constant rate, so a linear fit was applied to the data, and the slope was determined to be 12.8°/frame, with $R^2=0.999$. The deduced angular velocity was 128°/s, in good agreement with the measured angular velocity of 120±4°/s, indicating that the movie provided a reliable representation of the movement of the phantom.

Figure 45:
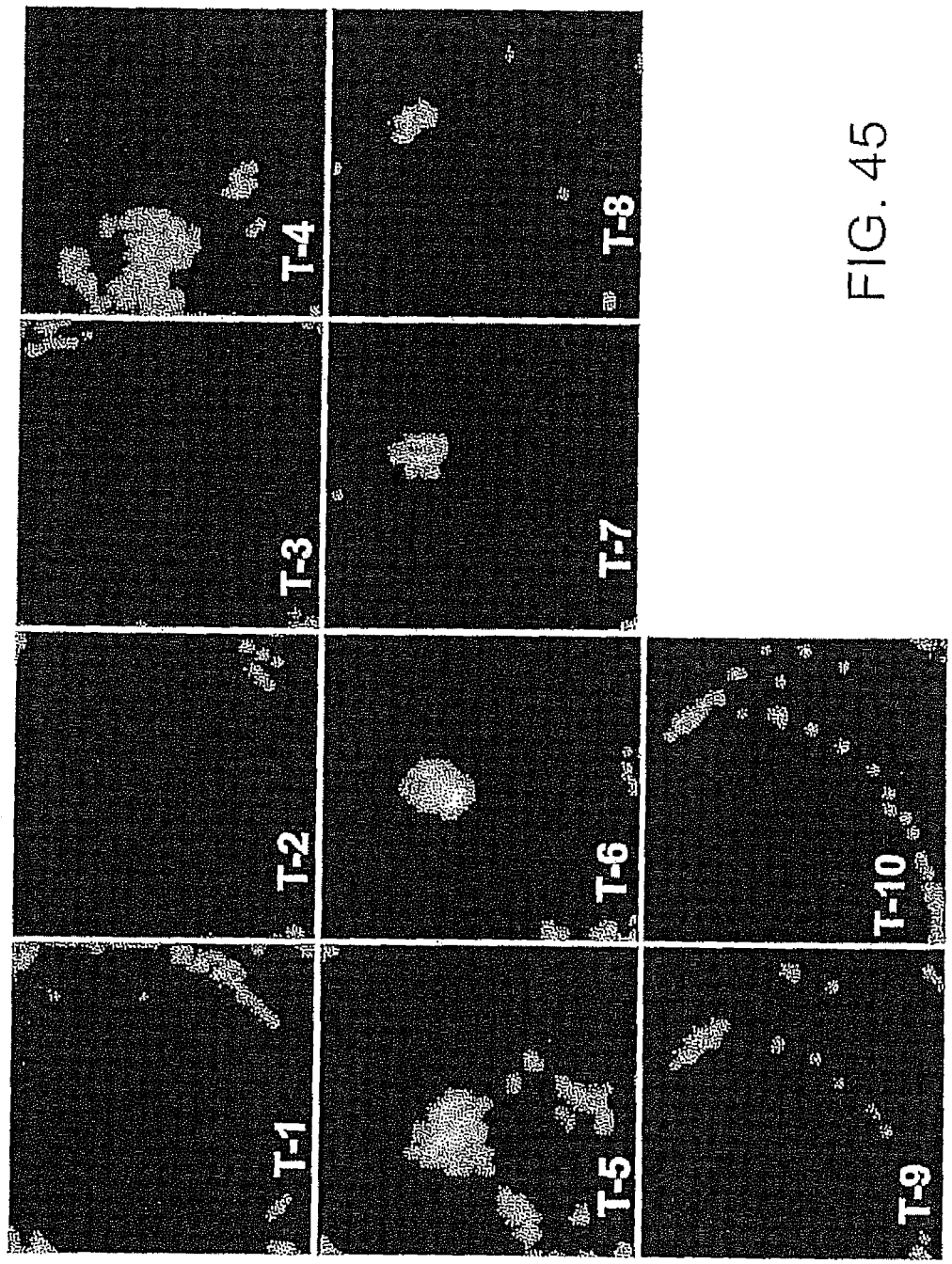
FIG. 45 is a 3-D PA image of a live mouse injected with optically absorbing dye and imaged with a twelve detector sparse array, presented as a sequence of ten 2-D slices.

FIG. 45 is a 3D photoacoustic image acquired with a 12 detector sparse array similar to the sparse array shown in FIG. 5. An SKH1 mouse was anesthetized by inhaled isoflurane at 2% through a nose cone. The mouse was injected subcutaneously into the left hind flank with 50 µL of gold nanorod solution (an optical contrast agent) in isotonic saline solution with a hypodermic needle. The mouse was placed on the 3-D photoacoustic imaging apparatus with the injected hind flank facing the transducer array with water as a acoustic coupling agent. The 3-D image was collected with a field of view of 40×40×10 mm with a voxel size of 1×1×1 mm. Acquisition time was 1 second which corresponded to 10 pulses at 800 nm. The 3-D image is presented as a sequence of xy slices marked T-1 through T-10 with T-1 representing a position inside the mouse and T-10 a position outside the animal and closest to the transducer array. Slices T-2 through T-9 represent intermediate xy slices for the range of distances from the transducer array intermediate to T-1 and T-10. Images T-5 and T-6 show the reconstructed subcutaneous bleb of gold nanorod solution as bright features near the center of each image. Images T-7 and T-8 show the needle track of gold nanorods that was left behind inside the mouse upon withdrawal of the hypodermic needle. Image analysis indicated that the area of the bright spot discernable in images T-5 and T-6 was approximately 25 square mm, which corresponds to the injected volume of 50 µL given the slice thickness.

One skilled in the art will recognize that acoustically refractive and attenuating objects placed between the image volume and the transducer array can be accounted for by the methods described above. The basic method would involve two steps. The first step is to perform a calibration scan with the refractive and attenuating object absent. The results of the calibration scan are used to determine the location of the transducer elements as described above and referenced in FIG. 30 If sufficient prior knowledge of the transducer positions is in hand then this step is not necessary. The refractive object can be then placed back onto to the imaging system and a second calibration scan collected. Image reconstructions of PA sources with the refractive object present, that use the detector positions determined from the first calibration scan (optional), and that use the parameters for the basis functions determined from the second calibration scan will be accurately reconstructed.

An example of an acoustically refractive and attenuating object is an optically clear plastic holder for restraining a mouse during the imaging procedure. This holder may be made from other materials that are optically clear or translucent. Without the corrective image reconstruction procedure described above the holder would refract and attenuate the PA signals in a manner that would render the image reconstruction based on *Paltauf et al.* unusable. The holder is a useful device since it immobilizes the subject and can be removed and transported to other imaging modalities (e.g. MRI, x-ray CT, PET/CT, SPECT/CT, etc). By foreknowledge of the relative position of the holder within the so produced images, co-registration of images between imaging modalities is accomplished. This is enhanced in some instances when the position of the holder is visible in the images (e.g. x-ray CT) or made visible by fiducial marks (e.g. water-filled inclusions for MRI). Therefore, this reconstruction method in combination with the holder enables co-registered multimodality images to be collected from the same immobilized specimen.

It will be appreciated that the apparatus, method and systems described above have a wide variety of applications. The present PA imaging method and system can be used for tumor detection and characterization in humans, including breast cancer. The system is also suitable for imaging real-time bio-distribution of drugs attached to optically absorbing tracers. Also, the present method and system can be used to provide 3-D imaging of a reaction proceeding in a chemical reactor for process monitoring, assessment of mixing, etc. Also, blood flow parameters in real-time at individual vessels using bolus injection of PA contrast agent, can be imaged using the present system and method. Furthermore, it is possible to image real-time distribution of optically absorbing substances in vitro which can be particularly useful in the pharmaceutical industry.

It will be appreciated by those skilled in the art that the present imaging system can also be integrated with MRI systems for co-registered imaging of blood vessels and soft tissue. It is also possible to integrate the present PA imaging system with a CT system for co-registered imaging of physiological and structural information. By integrating the present PA imaging system with a PET system, it is possible to provide co-registered imaging of physiological and molecular and metabolic information. Other combinations are also possible such as a PAI, PET/CT system for co-registered imaging of structural, physiological, molecular and metabolic information.

It will be appreciated by those skilled in this art that various modifications and changes are possible to the described apparatus and systems without departing from the spirit and scope of this invention. Accordingly, all such modifications and changes are intended to be part of this invention.

We claim:

1. Apparatus for photoacoustic (PA) imaging of a subject, said apparatus comprising:
   a light positioned to illuminate said subject to generate PA waves emanating from said subject;
   a programmed computer system;
   a staring array of transducers for receiving said PA waves and converting said PA waves to corresponding analog signals, said staring array having at least three transducers and arranged in at least three dimensions and wherein three-dimensional (3-D) spatial co-ordinates of the transducers is to be determined by the programmed computer system;
   an acoustically transmissive medium which surrounds the transducers and acoustically couples said staring array to said subject;

at least one analog to digital converter configured to receive said analog signals and convert said analog signals to corresponding digital signals; and the programmed computer system operatively connected to said at least one analog to digital converter to receive said digital signals and configured to:

calibrate, at least when 3D spatial co-ordinates of the transducers is to be determined by the programmed computer system, the acoustic response of each of the transducers by measurements of PA waves from a PA source at a known plurality of positions, predetermined by the programmed computer system, through a calibration volume to generate at least three-dimensional (3-D) characterization maps for each transducer, and process said digital signals, received when the staring array is staring, by an image reconstruction algorithm to create one or more three dimensional (3-D) images of said subject, said image reconstruction algorithm utilizes the three-dimensional (3-D) characterization maps for at least some of the transducers.

2. An apparatus according to claim 1 wherein said light comprises a laser capable of providing a pulsed laser beam.

3. An apparatus according to claim 2 including at least one photo detector, comprising a photo diode, configured to detect the illumination from said pulsed laser beam and providing digital signals indicative thereof to said computer system.

4. An apparatus according to claim 3 further comprising a relatively thin, optically transparent, window formed of acoustically transparent material for separating said subject from said staring array, wherein, during use of said apparatus, the illumination from said laser beam passes through said relatively thin, optically transparent, acoustically transparent window in order to illuminate said subject and said PA waves from said subject pass through said relatively thin, optically transparent, acoustically transparent material to said staring array.

5. An apparatus according to claim 2 wherein said laser is tunable.

6. An apparatus according to claim 1 wherein said light is located to illuminate said subject from a same side of the subject as a side on which said staring array is located.

7. An apparatus according to claim 1 wherein said staring array is an annular array, further comprising a supporting structure including an annular holder having said transducers distributed around an annular surface of said annular holder and defining a central hole, and said central hole is covered by an optical window made of an optically transparent material.

8. An apparatus according to claim 7 wherein said annular holder includes an annular wedge-shaped section having a flat annular side on which said transducers are mounted and creating a focal zone above a center of said staring array and wherein, during use of said apparatus, said PA waves are refracted by said wedge-shaped section before being transmitted to said transducers.

9. An apparatus according to claim 1 wherein said staring array is a hemispherical array, further comprising a supporting structure includes a plurality of transducer mounts each having one or more transducers mounted thereon at predetermined elevation angles, and said transducer mounts are arranged in a circle around a central hole which is covered by an optical window made of an optically transparent material.

10. An apparatus according to claim 1 further comprising a supporting structure for mounting said staring array wherein said staring array and said supporting structure are part of a transportable device which can be held in a user's hand during use of the apparatus.

11. An apparatus according to claim 1 further comprising a tank which holds the acoustically transmissive medium.

12. An apparatus according to claim 3 wherein said computer system is configured to normalize said digital signals to measured illumination.

13. An apparatus according to claim 2 wherein said computer system is operatively connected to said laser and programmed to control said laser, and said computer system is also programmed to coordinate the operation of said at least one analog to digital converter with the operation of said laser.

14. An apparatus according to claim 1 wherein said image reconstruction algorithm is an iterative forward projecting, back projecting image reconstruction algorithm.

15. An apparatus according to claim 1, further comprising:
a laser source configured to produce a pulsed laser beam;
an optical fiber configured to receive said pulsed laser beam and generate said PA waves as said PA source at one end of said optical fiber when a pulse of laser beam illuminates said optical fiber; and
a scanner configured to move at least a portion of said optical fiber through the calibration volume.

16. An apparatus according to claim 15 wherein said one end of the optical fiber comprises an opaque coated tip of the optical fiber.

17. An apparatus according to claim 1 wherein said image reconstruction algorithm reconstructs the one or more three dimensional (3-D) images of said subject based on received corresponding digital signals for at least some but not all of the transducers.

18. An apparatus according to claim 17 wherein said image reconstruction algorithm reconstructs the one or more three dimensional (3-D) images of said subject using the three-dimensional (3-D) characterization maps for at least some but not all of the transducers due to additional material located between said subject and which interfere with coupling of said PA waves from said subject to at least one of the remaining transducers.

19. An apparatus according to claim 17 wherein said image reconstruction algorithm reconstructs the one or more three dimensional (3-D) images of said subject using the three-dimensional (3-D) characterization maps for at least some but not all of the transducers due to missing or incomplete data associated with at least one of the remaining transducers.

20. An apparatus according to claim 1 wherein the 3-D characterization maps includes, specific to each pair comprising a respective one of said transducers and said PA source position, at least one or all of: estimates of time of flight of said PA waves, amplitude of said PA waves, temporal width of said PA waves, shape of said PA waves, dampening of said PA waves, and frequency content of said PA waves.

21. An apparatus according to claim 1 wherein the staring array further comprises a staring sparse array, wherein said transducers are spaced apart from one another in order to provide a wider range of viewing angles of said subject compared to viewing angles achievable with an equivalent number of closer spaced transducers and without said calibration.

22. A method for photoacoustic (PA) imaging of a subject using a staring array of transducers for receiving said PA waves and converting said PA waves to corresponding signals, said staring array having at least three transducers and arranged in at least three dimensions and wherein three-dimensional (3-D) spatial co-ordinates of the transducers is to be determined by a programmed computer system, and an acoustically transmissive medium which surrounds the transducers and acoustically couples said staring array to said subject, said method comprising:

calibrating, at least when 3D spatial co-ordinates of the transducers is to be determined by the programmed computer system, the acoustic response of each of the transducers by measurements of PA waves from a PA source at a known plurality of positions, predetermined by the programmed computer system, through a calibration volume, and generating three-dimensional (3-D) characterization maps for each transducer, and estimating a position of each transducer element relative to the calibration volume;

illuminating said subject to generate PA waves emanating from said subject;

creating, based on signals received from the transducers when the staring array is staring, and utilizing the three-dimensional (3-D) characterization maps for at least some of the transducers, one or more three dimensional (3-D) images of said subject.

23. A method according to claim 22 wherein said PA source comprises a laser capable of providing a pulsed laser beam.

24. A method according to claim 22 wherein the said generating the 3-D characterization maps includes providing at least one or all of: estimates of time of flight of said PA waves, amplitude of said PA waves, temporal width of said PA waves, shape of said PA waves, dampening of said PA waves, and frequency content of said PA waves, specific to each pair comprising a respective one of said transducers and said PA source position.

25. A method according claim 22 wherein said generating the 3-D characterization maps includes calculating properties of said array, including number of said transducers sensitive to each grid point, angular acceptance of said transducers, and number of said grid points where PA waves are detectable for each transducer.

26. A method according to claim 23 including recording the power of each laser pulse, and monitoring fluctuations in the power of the pulses of the laser beam.

27. A method according to claim 22 wherein the staring array further includes a staring sparse array, wherein said transducers are spaced apart from one another in order to provide a wider range of viewing angles of said subject compared to viewing angles achievable with an equivalent number of closer spaced transducers and without said calibrating.

* * * * *